United States Patent
Taniguchi

(10) Patent No.: US 11,801,505 B2
(45) Date of Patent: Oct. 31, 2023

(54) STRONG CATION EXCHANGE CHROMATOGRAPHIC MATRIX AND METHOD FOR USING SAME

(71) Applicant: ASAHI KASEI MEDICAL CO., LTD., Tokyo (JP)

(72) Inventor: Hiroki Taniguchi, Tokyo (JP)

(73) Assignee: ASAHI KASEI MEDICAL CO., LTD., Tokyo (JP)

(*) Notice: Subject to any disclaimer, the term of this patent is extended or adjusted under 35 U.S.C. 154(b) by 0 days.

(21) Appl. No.: 17/570,891

(22) Filed: Jan. 7, 2022

(65) Prior Publication Data

US 2022/0126282 A1 Apr. 28, 2022

Related U.S. Application Data

(62) Division of application No. 16/331,262, filed as application No. PCT/JP2017/032275 on Sep. 7, 2017, now abandoned.

(30) Foreign Application Priority Data

Sep. 9, 2016 (JP) .................................. 2016-176951
Nov. 2, 2016 (JP) .................................. 2016-215052

(51) Int. Cl.
*B01D 15/18* (2006.01)
*B01D 15/36* (2006.01)
(Continued)

(52) U.S. Cl.
CPC .......... *B01J 39/26* (2013.01); *B01D 15/1871* (2013.01); *B01D 15/36* (2013.01); *B01D 15/362* (2013.01);
(Continued)

(58) Field of Classification Search
CPC ... B01J 39/26; B01J 39/05; B01J 39/07; B01J 39/20; B01J 47/127; B01J 47/12;
(Continued)

(56) References Cited

U.S. PATENT DOCUMENTS 6,428,704 B1 8/2002 Setoguchi et al.
2007/0102364 A1 5/2007 Okada et al.
(Continued)

FOREIGN PATENT DOCUMENTS

CN 101451158 6/2009
CN 101791540 8/2010
(Continued)

OTHER PUBLICATIONS

Kim M et al: "Ring-opening reaction of poly-GMA chain grafted onto a porous membrane", J. Membrane Sci., Elsevier BV, NL, vol. 117, No. 1, Aug. 21, 1996 (Aug. 21, 1996), pp. 33-3.
(Continued)

*Primary Examiner* — Benjamin L Lebron
(74) *Attorney, Agent, or Firm* — GREENBLUM & BERNSTEIN P.L.C.

(57) ABSTRACT

A cation exchange chromatographic matrix comprising a base material, and a copolymer with one monomer unit having at least a sulfonic acid group, the copolymer being immobilized on the base material, wherein: the copolymer forms substantially no cross-linked structure, and the copolymer comprises neither acrylamide nor an acrylamide derivative as a monomer unit, or comprises acrylamide or an acrylamide derivative as a monomer unit in a range which has no substantial influence; the ratio of the mass of the copolymer to the mass of the base material is 5% or more and 200% or less; and the density of the sulfonic acid group is higher than 30 mmol/L and 200 mmol/L or lower.

26 Claims, 9 Drawing Sheets

(51) Int. Cl.

| | |
|---|---|
| *B01D 15/38* | (2006.01) |
| *B01J 39/05* | (2017.01) |
| *B01J 39/20* | (2006.01) |
| *B01J 39/26* | (2006.01) |
| *C07K 1/18* | (2006.01) |
| *C07K 1/22* | (2006.01) |
| *C07K 16/00* | (2006.01) |
| *C08F 255/02* | (2006.01) |
| *C08J 5/22* | (2006.01) |
| *B01J 39/07* | (2017.01) |
| *B01J 47/12* | (2017.01) |
| *G01N 30/02* | (2006.01) |
| *G01N 30/88* | (2006.01) |
| *B01J 47/127* | (2017.01) |

(52) U.S. Cl.
CPC ....... *B01D 15/363* (2013.01); *B01D 15/3809* (2013.01); *B01J 39/05* (2017.01); *B01J 39/07* (2017.01); *B01J 39/20* (2013.01); *B01J 47/12* (2013.01); *B01J 47/127* (2017.01); *C07K 1/18* (2013.01); *C07K 1/22* (2013.01); *C07K 16/00* (2013.01); *C08F 255/02* (2013.01); *C08F 255/023* (2013.01); *C08J 5/22* (2013.01); *C08J 5/2287* (2013.01); *G01N 30/02* (2013.01); *G01N 30/88* (2013.01)

(58) Field of Classification Search
CPC .. B01D 15/1871; B01D 15/36; B01D 15/362; B01D 15/363; B01D 15/3809; C07K 1/18; C07K 1/22; C07K 16/00; C08F 255/02; C08F 255/023; C08J 5/22; C08J 5/2287; G01N 30/02; G01N 30/88
See application file for complete search history.

(56) References Cited

U.S. PATENT DOCUMENTS

| | | |
|---|---|---|
| 2012/0123002 A1 | 5/2012 | Shinohara |
| 2012/0178910 A1 | 7/2012 | Arunakumari et al. |
| 2013/0245139 A1 | 9/2013 | Kozlov et al. |
| 2013/0317129 A1* | 11/2013 | Koguma .............. B01J 20/3278 521/38 |
| 2013/1317129 | 11/2013 | Koguma |
| 2015/0133618 A1 | 5/2015 | Hanssen et al. |
| 2015/0266919 A1 | 9/2015 | Ishihara et al. |
| 2016/0083419 A1 | 3/2016 | Taniguchi et al. |
| 2017/0145050 A1 | 5/2017 | Taniguchi et al. |

FOREIGN PATENT DOCUMENTS

| | | |
|---|---|---|
| JP | S63-232845 | 9/1988 |
| JP | 2012-224729 | 11/2012 |
| JP | 2013-178272 | 9/2013 |
| JP | 2013-189427 | 9/2013 |
| JP | 2014-020830 | 2/2014 |
| JP | 2015-515633 | 5/2015 |
| WO | 2003/049671 | 6/2003 |
| WO | 2013/162449 | 10/2013 |
| WO | 2014/061411 | 4/2014 |
| WO | 2014/134147 | 9/2014 |
| WO | 2014/171437 | 10/2014 |
| WO | 2015/088677 | 6/2015 |
| WO | 2016/013609 | 1/2016 |
| WO | 2016/093251 | 6/2016 |

OTHER PUBLICATIONS

Supplementary European Search Report, European Patent Office, Application No. 17848844.1, dated Aug. 21, 2019, 5 pages.
Anonymous: "Hydrophilicity: Gold Book" in: "IUPAC Compendium of Chemical Terminology", Feb. 24, 2014.
"Ring-opening reaction of poly-GMA chain grafted onto a porous membrane", Min Kim et al., Journal of Membrane Science, vol. 117, pp. 33-38, Dec. 1996.

* cited by examiner

Fig. 3

| | Antibody throughput / membrane volume(mg/mL) | Before treatment (content ratio) | | | After treatment (content ratio) | | | Monomer recovery rate | Aggregate ratio reduction rate |
|---|---|---|---|---|---|---|---|---|---|
| | | Aggregate component(1) | Aggregate component(2) | Monomer component(3) | Aggregate component(1) | Aggregate component(2) | Monomer component(3) | | |
| Example1 | 893 | 2.35% | 1.92% | 95.73% | 0.28% | 0.52% | 99.20% | 93% | 81% |
| Example2 | 927 | 2.13% | 1.95% | 95.92% | 0.25% | 0.51% | 99.24% | 93% | 81% |
| Example3 | 742 | 2.06% | 1.77% | 96.17% | 0.12% | 0.56% | 99.32% | 93% | 82% |
| Example4 | 1141 | 3.77% | 2.38% | 93.85% | 0.05% | 0.51% | 99.44% | 90% | 91% |
| Example5 | 1142 | 1.91% | 2.30% | 95.79% | 0.00% | 0.30% | 99.70% | 92% | 93% |
| Example6 | 1192 | 1.77% | 2.24% | 95.93% | 0.00% | 0.50% | 99.50% | 96% | 88% |
| Example7 | 1182 | 1.71% | 2.01% | 96.23% | 0.03% | 0.79% | 99.18% | 96% | 78% |
| Example8 | 1139 | 2.72% | 2.19% | 95.09% | 0.00% | 0.29% | 99.71% | 91% | 94% |
| Example9 | 2354 | 0.70% | 1.37% | 97.93% | 0.00% | 0.42% | 99.58% | 95% | 80% |
| Example10 | 1114 | 3.04% | 2.13% | 94.83% | 0.00% | 0.31% | 99.69% | 90% | 94% |
| Example11 | 1134 | 2.20% | 1.97% | 95.83% | 0.00% | 0.65% | 99.35% | 93% | 84% |
| Example12 | 922 | 2.15% | 1.78% | 96.07% | 0.00% | 0.26% | 99.74% | 90% | 93% |
| Example13 | 907 | 0.56% | 1.58% | 97.83% | 0.00% | 0.49% | 99.51% | 85% | 77% |
| Example14 | 592 | 0.97% | 2.50% | 96.53% | 0.02% | 0.41% | 99.57% | 82% | 88% |
| Example15 | 755 | 0.42% | 1.75% | 97.83% | 0.00% | 0.41% | 99.59% | 92% | 81% |
| Example16 | 550 | 1.99% | 2.59% | 95.42% | 0.16% | 0.46% | 99.38% | 83% | 86% |
| Example17 | 756 | 1.04% | 2.88% | 96.03% | 0.00% | 0.58% | 99.42% | 94% | 85% |
| Comparative Example1 | 871 | 1.76% | 2.17% | 96.07% | 1.38% | 2.01% | 96.61% | 97% | 14% |
| Comparative Example2 | 863 | 2.65% | 2.21% | 95.14% | 1.63% | 1.61% | 96.76% | 95% | 33% |
| Comparative Example3 | 826 | 2.17% | 1.87% | 95.93% | 1.45% | 1.66% | 96.89% | 95% | 23% |
| Comparative Example4 | 812 | 2.22% | 1.98% | 95.80% | 1.55% | 1.78% | 96.67% | 93% | 21% |

Fig. 4

|  | Cation exchange membrane5 | Cation exchange membrane6 | Cation exchange membrane7 | Cation exchange membrane8 | Cation exchange membrane9 | Cation exchange membrane10 | Cation exchange membrane11 | Cation exchange membrane12 | Cation exchange membrane13 |
|---|---|---|---|---|---|---|---|---|---|
| 2-Hydroxyethyl methacrylate | 7.46g | 7.27g | 6.87g | 6.68g | 5.50g | 5.10g | 4.71g | 4.08g | 2.72g |
| Glycidyl methacrylate | 0.39g | 0.59g | 0.98g | 1.18g | 0.72g | 0.69g | 0.66g | 0.55g | 0.37g |
| Methanol | 113mL | 113mL | 113mL | 113mL | 114mL | 115mL | 115mL | 116mL | 117mL |
| Graft rate | 101% | 93% | 96% | 109% | 84% | 77% | 72% | 61% | 41% |
| Sulfonic acid group density | 66mmol/L | 83mmol/L | 128mmol/L | 142mmol/L | 93mmol/L | 95mmol/L | 94mmol/L | 78mmol/L | 55mmol/L |
| Mass of monomer unit having sulfonic acid group / mass of monomer unit having no charge | 1/9.84 | 1/7.13 | 1/4.17 | 1/3.66 | 1/6.14 | 1/5.87 | 1/5.71 | 1/5.74 | 1/5.84 |
| Graft chain density(g/mL) | 0.154 | 0.150 | 0.149 | 0.147 | 0.154 | 0.147 | 0.144 | 0.122 | 0.088 |

Fig. 5

| | Antibody throughput/ membrane volume(mg/mL) | Before treatment (content ratio) | | | After treatment (content ratio) | | | Monomer recovery rate | Aggregate ratio reduction rate |
|---|---|---|---|---|---|---|---|---|---|
| | | Aggregate component(1) | Aggregate component(2) | Monomer component(3) | Aggregate component(1) | Aggregate component(2) | Monomer component(3) | | |
| Cation exchange membrane 4 | 637 | 2.86% | 2.43% | 94.71% | 0.04% | 0.63% | 99.33% | 92% | 87% |
| Cation exchange membrane 5 | 655 | 2.61% | 2.35% | 95.04% | 0.12% | 0.54% | 99.34% | 91% | 87% |
| Cation exchange membrane 6 | 742 | 4.14% | 2.64% | 93.22% | 0.23% | 0.77% | 99.00% | 89% | 85% |
| Cation exchange membrane 7 | 686 | 2.78% | 2.45% | 94.77% | 0.08% | 0.42% | 99.50% | 86% | 90% |
| Cation exchange membrane 8 | 1021 | 2.65% | 2.54% | 94.81% | 0.03% | 0.25% | 99.75% | 88% | 95% |
| Cation exchange membrane 9 | 1034 | 2.58% | 2.48% | 94.94% | 0.03% | 0.27% | 99.73% | 90% | 95% |
| Cation exchange membrane 10 | 1028 | 2.57% | 2.51% | 94.92% | 0.03% | 0.27% | 99.73% | 89% | 95% |
| Cation exchange membrane 11 | 1023 | 2.68% | 2.21% | 95.11% | 0.09% | 0.49% | 99.42% | 90% | 88% |
| Cation exchange membrane 12 | 1012 | 2.77% | 2.39% | 94.84% | 0.83% | 0.91% | 98.26% | 92% | 66% |

Fig. 6

| | Antibody throughput / membrane volume[mg/mL] | Before treatment (content ratio) | | | After treatment (content ratio) | | | Monomer recovery rate | Aggregate ratio reduction rate |
|---|---|---|---|---|---|---|---|---|---|
| | | Aggregate component (1) | Aggregate component (2) | Monomer component (3) | Aggregate component (1) | Aggregate component (2) | Monomer component (3) | | |
| Example20 | 743 | 2.75% | 2.01% | 95.24% | 0.18% | 0.51% | 99.31% | 90% | 86% |
| Example21 | 781 | 1.35% | 1.53% | 97.12% | 0.21% | 0.53% | 99.26% | 83% | 74% |

Fig. 7

| | Antibody throughput / membrane volume (mg/mL) | Before treatment (content ratio) | | | After treatment (content ratio) | | | Monomer recovery rate | Aggregate ratio reduction rate | HCP reduction rate Protein A reduction rate |
|---|---|---|---|---|---|---|---|---|---|---|
| | | Aggregate component (1) | Monomer component (2) | Monomer component (3) | Aggregate component (1) | Aggregate component (2) | Monomer component (3) | | | |
| pH5.0 | 683 | 2.44% | 2.13% | 95.43% | 0.12% | 0.45% | 99.43% | 89% | 88% | HCP:92% ProteinA:81% |
| | | HCP:527ppm, Protein A:2.2ppm | | | HCP:43.8ppm, Protein A:0.4ppm | | | | | |
| pH6.0 | 771 | 2.73% | 2.31% | 94.96% | 0.12% | 0.42% | 99.46% | 90% | 89% | HCP:83% ProteinA:72% |
| | | HCP:478ppm, Protein A:2.7ppm | | | HCP:p78.9ppm, Protein A:0.8ppm | | | | | |
| pH7.0 | 961 | 2.62% | 2.03% | 95.35% | 0.07% | 0.28% | 99.65% | 90% | 92% | HCP:79% ProteinA:64% |
| | | HCP:326ppm, Protein A:2.3ppm | | | HCP:67.4ppm, Protein A:0.8ppm | | | | | |

Fig. 8

| Example23 | | Aggregate component(1) | Aggregate component(2) | Monomer component(3) | | HCP | Protein A |
|---|---|---|---|---|---|---|---|
| | After affinity chromatography step | 1.35% | 0.77% | 97.87% | | 230ppm | 3ppm |
| | Cation exchange step: antibody throughput / support volume = 1082mg/mL Monomer recovery rate 88% | | | | | | |
| | After cation exchange chromatography step | 0% | 0.06% | 99.94% | | 49ppm | <1ppm |
| | Anion exchange step: antibody throughput/ support volume = 2963mg/mL Monomer recovery rate 99% | | | | | | |
| | After anion exchange chromatography step | 0% | 0.05% | 99.95% | | 3ppm | <1ppm |

| Example24 | | Aggregate component(1) | Aggregate component(2) | Monomer component(3) | | HCP | Protein A |
|---|---|---|---|---|---|---|---|
| | After affinity chromatography step | 1.70% | 1.89% | 96.41% | | 307ppm | 3ppm |
| | Cation exchange step: antibody throughput / support volume = 1227mg/mL Monomer recovery rate 90% | | | | | | |
| | After cation exchange chromatography step | 0% | 0.18% | 99.82% | | 108ppm | <1ppm |
| | Anion exchange step: antibody throughput/ support volume = 2937mg/mL Monomer recovery rate 96% | | | | | | |
| | After anion exchange chromatography step | 0% | 0.18% | 99.82% | | 4ppm | <1ppm |

| Example25 | | Aggregate component(1) | Aggregate component(2) | Monomer component(3) | | HCP | Protein A |
|---|---|---|---|---|---|---|---|
| | After affinity chromatography step | 1.72% | 1.80% | 96.48% | | 319ppm | 3ppm |
| | Cation exchange step: antibody throughput / support volume = 1212mg/mL Monomer recovery rate 91% | | | | | | |
| | After cation exchange chromatography step | 0% | 0.19% | 99.81% | | 108ppm | <1ppm |
| | Anion exchange step: antibody throughput/ support volume = 4083mg/mL Monomer recovery rate 98% | | | | | | |
| | After anion exchange chromatography step | 0% | 0.19% | 99.81% | | 5ppm | <1ppm |

Fig. 9

| | | Aggregate component(1) | Aggregate component(2) | Monomer component(3) | | HCP | Protein A |
|---|---|---|---|---|---|---|---|
| | After affinity chromatography step | 1.45% | 1.18% | 97.37% | | 238ppm | 3ppm |
| Example26 | Ion exchange step at pH 5.0: antibody throughput: 203mg | 0% | 0.18% | 99.82% | Monomer recovery rate 92% | 7ppm | <1ppm |
| | After ion exchange chromatography step | | | | | | |
| | Ion exchange step at pH 6.0: antibody throughput: 306mg | 0% | 0.06% | 99.94% | Monomer recovery rate 88% | 5ppm | <1ppm |
| | After ion exchange chromatography step | | | | | | |
| | Ion exchange step at pH 7.0: antibody throughput: 317mg | 0% | 0.05% | 99.95% | Monomer recovery rate 89% | 5ppm | <1ppm |
| | After ion exchange chromatography step | | | | | | |
| | Ion exchange step at pH 8.0: antibody throughput: 309mg | 0% | 0.08% | 99.92% | Monomer recovery rate 90% | 4ppm | <1ppm |
| | After ion exchange chromatography step | | | | | | | ature-responsive monomer and a graft chain having a strong
STRONG CATION EXCHANGE CHROMATOGRAPHIC MATRIX AND METHOD FOR USING SAME

CROSS-REFERENCE TO RELATED APPLICATIONS

This application is a Divisional of U.S. application Ser. No. 16/331,262, filed on Mar. 7, 2019, which is a National Stage of International Application No. PCT/JP2017/032275, filed on Sep. 7, 2017, which claims priority to Japanese Application No. 2016-215052, filed Nov. 2, 2016 and Japanese Application No. 2016-176951, filed Sep. 9, 2016. The disclosures of which are expressly incorporated by reference herein in their entireties.

TECHNICAL FIELD

The present invention relates to an ion exchange chromatographic matrix having a strong cation exchange group, and a method for purifying a biomolecule using the same.

BACKGROUND ART

Immunoglobulins (antibodies) are physiologically active substances responsible for immune response. In recent years, their utility value has increased for purposes such as drugs, diagnostics, or separation or purification materials for corresponding antigenic proteins. The antibodies are obtained from the blood of immunized animals, cell culture solutions of cells having the capability to produce the antibodies, or ascitic fluid culture solutions of animals having such capability. However, the blood or the culture solutions containing the antibodies contain proteins other than the antibodies, or complicated impurities derived from raw material solutions used in the cell culture. Typically, a complicated operation that requires a long time is necessary for separating or purifying the antibodies from these impurity components.

Liquid chromatography is important for antibody separation or purification. Chromatography approaches for separating antibodies include gel filtration chromatography, affinity chromatography, ion exchange chromatography, and reverse-phase chromatography, etc. These approaches are combined to separate or purify antibodies.

The ion exchange chromatography is a method which performs separation by reversibly adsorbing a counterion present in a mobile phase with an ion exchange group on adsorbent surface as a stationary phase. For example, beads, flat membranes, and hollow fiber membranes are adopted as shapes of the adsorbent. Such base materials bonded to a cation exchange group or an anion exchange group are commercially available as adsorbents.

For the adsorbent having a cation exchange group, purification is generally performed by contacting an antibody solution having a low salt concentration with the adsorbent to adsorb the antibody thereto, and elevating the salt concentration of the mobile phase to elute the adsorbed antibody. In addition, the purification of a target substance in a flow-through mode described below has also been proposed as a more favorable method.

The flow-through mode is a mode of a purification method for selectively adsorbing impurities, rather than the target substance, to an adsorbent. Hence, this approach leads to savings of buffer solutions or simplification of a process as compared with the conventional methods using adsorption and elution. If an antibody solution can be treated at a high flow rate, it is considered that the advantages of the flow-through purification can be further exploited.

A cation exchange step often intends to separate an antibody monomer from aggregates such as an antibody dimer. However, the antibody monomer has an isoelectric point almost equal to that of the antibody aggregates. Therefore, the flow-through purification particularly has the difficulty in separating the antibody monomer from the antibody dimer. Thus, it is necessary to carefully design a cation exchanger.

Patent Literature 1 discloses a chromatographic matrix suitable for flow-through purification, wherein a monomer having a strong cation exchange group and an uncharged monomer are graft-polymerized to a matrix.

Patent Literature 2 discloses a chromatographic matrix suitable for flow-through purification, wherein a temperature-responsive monomer and a graft chain having a strong cation exchange group are immobilized on a matrix.

Patent Literature 3 discloses a chromatographic matrix suitable for flow-through purification, the chromatographic matrix having a weak cation exchange group.

CITATION LIST

Patent Literature

Patent Literature 1: Japanese Patent Laid-Open No. 2013-189427
Patent Literature 2: International Publication No. WO 2014/171437
Patent Literature 3: International Publication No. WO 2016/013609

SUMMARY OF INVENTION

Technical Problem

The cation exchanger disclosed in Patent Literature 1 is characterized in use of a cation exchange group having a low density (1 to 30 mmol/L) on a solid matrix. A higher density of the cation exchange group fails to efficiently remove aggregates in flow-through purification. Therefore, there is a limitation on the density of the cation exchange group. Hence, the amount of antibodies that can be purified is not always large.

The cation exchanger disclosed in Patent Literature 2 contains a temperature-responsive monomer acrylamide derivative, specifically, isopropylacrylamide, as a monomer unit in the graft chain. Therefore, its purification capability tends to be influenced by temperature. Furthermore, at a low treatment temperature, the polymer chain containing isopropylacrylamide as a monomer unit becomes hydrophilic so that aggregate removal capability is reduced. Hence, a hydrophobic monomer is copolymerized with the isopropylacrylamide to decrease the lower-limit critical temperature of the copolymer. Such strengthened hydrophobic properties of the polymer improve aggregate removal capability around room temperature. However, precise temperature control is necessary for stabilizing the capability of the cation exchanger disclosed in Patent Literature 2. Meanwhile, the manufacture of protein drugs differs in temperature depending on a manufacturing site. Therefore, it is desirable to minimize the influence of temperature.

Furthermore, the cation exchange membrane having a cation exchange group density of 30 mmol/L or higher disclosed in Patent Literature 2 is susceptible to improvement in removal efficiency for antibody aggregates.

Patent Literature 3 discloses a cation exchange membrane suitable for flow-through purification, the cation exchange membrane having a cation exchange group density of 30 mmol/L or higher. The cation exchange membrane, albeit having a high cation exchange group density, can efficiently remove aggregates and can purify a large amount of antibodies. On the other hand, the disclosed cation exchange membrane mainly has a weak cation exchange group, and is susceptible to improvement from the viewpoint of the efficient removal of antibody aggregates in a wide pH range because the cation exchange group is not charged at low pH.

As mentioned above, none of the disclosed cation exchange membranes in the flow-through purification of physiologically active substances such as antibodies achieve efficient flow-through purification of a large amount of physiologically active substances in a wide pH range without being influenced by temperature. Accordingly, an object of the present invention is to provide a cation exchange membrane that is insusceptible to temperature in flow-through purification and is capable of efficiently purifying a large amount of physiologically active substances even at low pH.

Solution to Problem

The present inventor has conducted studies from various angles as well as research and development to attain the object. As a result, the present inventor has completed the present invention by finding the composition of a graft chain that is insusceptible to temperature in flow-through purification and is capable of efficiently purifying a large amount of physiologically active substances in a wide pH range.

According to an aspect, the present invention provides a cation exchange chromatographic matrix comprising a base material, and a copolymer with one monomer unit having at least a sulfonic acid group, the copolymer being immobilized on the base material, wherein: the copolymer forms substantially no cross-linked structure, and the copolymer comprises neither acrylamide nor an acrylamide derivative as a monomer unit, or comprises acrylamide or an acrylamide derivative as a monomer unit in a range which has no substantial influence; the ratio of the mass of the copolymer to the mass of the base material is 5% or more and 200% or less; and the density of the sulfonic acid group is higher than 30 mmol/L and 200 mmol/L or lower.

In the cation exchange chromatographic matrix described above, the molar ratio of the monomer unit having the sulfonic acid group in the copolymer may be smaller than the molar ratio of a neutral monomer unit having no charge.

In the cation exchange chromatographic matrix described above, the mass ratio of the monomer unit having the sulfonic acid group in the copolymer may be smaller than the mass ratio of a neutral monomer unit having no charge.

In the cation exchange chromatographic matrix described above, the monomer unit having the sulfonic acid group may be a glycidyl methacrylate derivative.

In the cation exchange chromatographic matrix described above, the neutral monomer unit may comprise at least a hydrophilic monomer unit, and the molar ratio of the hydrophilic monomer unit to the neutral monomer unit in the copolymer may be 50% or more.

In the cation exchange chromatographic matrix described above, the neutral monomer unit may comprise at least a hydrophilic monomer unit, and the ratio of the mass of the hydrophilic monomer unit to the total mass of the neutral monomer unit in the copolymer may be 50% or more.

The cation exchange chromatographic matrix described above may contain no carboxyl group, or may have a density of a carboxyl group lower than the density of the sulfonic acid group.

In the cation exchange chromatographic matrix described above, the base material may be in a membrane form.

According to an aspect, the present invention provides a cation exchange chromatographic matrix for biomolecule purification, comprising the cation exchange chromatographic matrix described above.

The cation exchange chromatographic matrix for biomolecule purification described above may be for antibody protein purification.

According to an aspect, the present invention provides a purification method for purifying a physiologically active substance from a mixed solution containing impurities and the physiologically active substance, comprising contacting the mixed solution with the cation exchange chromatographic matrix for biomolecule purification described above.

In the purification method described above, the mixed solution may be contacted with the matrix in a flow-through mode.

In the purification method described above, the pH of the mixed solution may be 4.0 or higher and 10.0 or lower.

In the purification method described above, the physiologically active substance may be a monomer of an antibody protein.

In the purification method described above, the impurities may include dimeric and higher aggregates of the antibody protein.

In the purification method described above, the recovery rate of the physiologically active substance may be 80% or more.

In the purification method described above, 100 mg or more of the antibody protein including the monomer and the aggregates may be purified per mL of the cation exchange chromatographic matrix for biomolecule purification.

In the purification method described above, the ratio of the aggregates may be reduced by 50% or more when a solution of the antibody protein including the monomer and the aggregates is purified.

The purification method described above may further comprise performing purification using an anion exchange chromatographic matrix before or after the purification step using the cation exchange chromatographic matrix.

In the purification method described above, the anion exchange chromatographic matrix may be in a membrane form.

In the purification method described above, the purification using an anion exchange chromatographic matrix may be a flow-through mode.

The purification method described above may further comprise an affinity chromatography step before the purification step using the cation exchange chromatographic matrix and the purification step using the anion exchange chromatographic matrix.

In the purification method described above, buffer replacement may not be performed in a series of purification steps.

In the purification method described above, the affinity chromatography step may be carried out in a bind and elute mode, and the physiologically active substance may be eluted with a buffer consisting of a monovalent acid in the elution step.

In the purification method described above, the electrical conductivity of the buffer consisting of a monovalent acid may be 10.0 mS/cm or lower.

The purification method described above may further comprise the step of adjusting the pH of the mixed solution to 4.0 or lower after the affinity chromatography step.

In the purification method described above, the electrical conductivity of the mixed solution containing the physiologically active substance may be 10 mS/cm or lower in a series of purification steps.

Advantageous Effects of Invention

Use of the cation exchange chromatographic matrix according to the present invention is insusceptible to temperature and achieves efficient flow-through purification of a large amount of physiologically active substances in a wide pH range.

BRIEF DESCRIPTION OF DRAWINGS

FIG. 3 is a table showing results of Examples 1 to 17 and Comparative Examples 1 to 4.

FIG. 4 is a table showing materials of a cation exchange membrane in Example 18.

FIG. 5 is a table showing results of Example 19.

FIG. 6 is a table showing results of Examples 20 and 21.

FIG. 7 is a table showing results of Example 22.

FIG. 8 is a table showing results of Examples 23 to 25.

FIG. 9 is a table showing results of Example 26.

DESCRIPTION OF EMBODIMENTS

Figure 1:
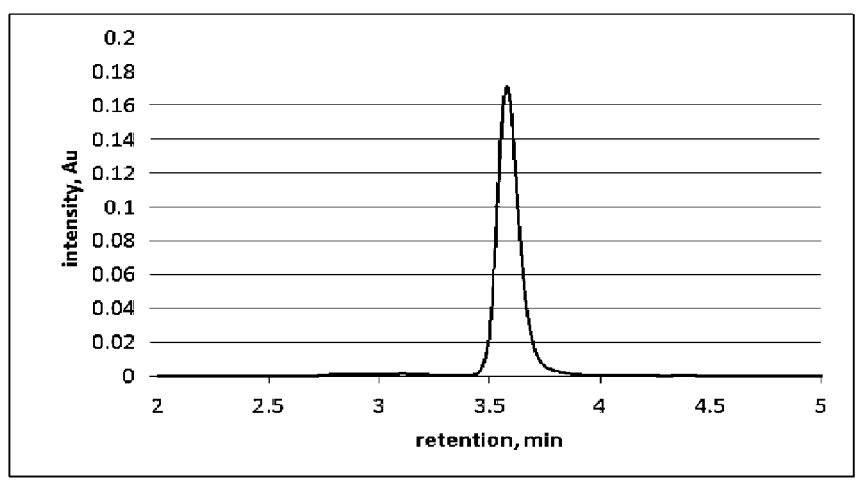
FIG. 1 is a chromatographic chart of absorbance when an antibody solution was assayed by size exclusion chromatography.

Hereinafter, the preferred mode for carrying out the present invention (hereinafter, referred to as the "embodiment") will be described in detail. The embodiment given below illustrates an apparatus or a method for embodying the technical idea of this invention. The technical idea of this invention is not limited to those described below in terms of combinations of constituent members, etc. For the technical idea of this invention, various changes or modifications can be made in the scope of claims.

The cation exchange chromatographic matrix according to the embodiment comprises a base material and a copolymer immobilized on the base material. One monomer unit of the copolymer has at least a sulfonic acid group. The copolymer forms substantially no cross-linked structure, and the copolymer comprises neither acrylamide nor an acrylamide derivative as a monomer unit, or comprises acrylamide or an acrylamide derivative as a monomer unit in a range which has no substantial influence. A graft rate which is the ratio of the mass of the copolymer to the mass of the base material is 5% or more and 200% or less. The density of the sulfonic acid group is higher than 30 mmol/L and 200 mmol/L or lower.

The cation exchange chromatographic matrix according to the embodiment is used, for example, in the purification of a physiologically active substance including impurities. The physiologically active substance is, for example, a monomer of an antibody protein. The impurities are, for example, dimeric and higher aggregates of the antibody protein.

The antibody protein, one example of the physiologically active substance, is a glycoprotein molecule (also referred to as a gamma globulin or an immunoglobulin) produced by B lymphocytes under a vertebrate defense mechanism against infection, as generally defined in biochemistry. For example, the antibody protein purified with the cation exchange chromatographic matrix according to the embodiment is used as a human drug and has substantially the same structure as that of the antibody protein present in vivo in a recipient human.

The antibody protein may be a human antibody protein or may be an antibody protein derived from a nonhuman mammal such as cattle or a mouse. Alternatively, the antibody protein may be a chimeric antibody protein with human IgG or a humanized antibody protein. The chimeric antibody protein with human IgG is an antibody protein having variable regions derived from a nonhuman organism such as a mouse and additionally having human-derived immunoglobulin constant regions replaced for nonhuman organism constant regions. The humanized antibody protein is an antibody protein having complementarity-determining regions (CDRs) derived from a nonhuman organism in variable regions and additionally having human-derived framework regions (FRs). The humanized antibody protein has lower immunogenicity than that of the chimeric antibody protein.

The antibody protein, one example of the target to be purified with the cation exchange chromatographic matrix according to the embodiment, is not particularly limited by its class (isotype) and subclass. For example, antibody proteins are classified according to structural difference in constant region into five families of classes: IgG, IgA, IgM, IgD, and IgE. However, the antibody protein which is the target to be purified with the cation exchange chromatographic matrix according to the embodiment may be any of the five families of classes. A human antibody protein IgG has 4 subclasses (IgG1 to IgG4), and IgA has 2 subclasses (IgA1 and IgA2). However, the antibody protein which is the target to be purified with the cation exchange chromatographic matrix according to the embodiment may be any of the subclasses. An antibody-related protein such as an Fc fusion protein comprising a protein bound with an Fc region may also be included in the antibody protein which is the target to be purified with the cation exchange chromatographic matrix according to the embodiment.

Antibody proteins can also be classified according to origin. However, the antibody protein which is the target to be purified with the cation exchange chromatographic matrix according to the embodiment may be any of a natural human antibody protein, a recombinant human antibody protein manufactured by a gene recombination technique, a monoclonal antibody protein, and a polyclonal antibody protein. Among these antibody proteins, the antibody protein which is the target to be purified with the cation exchange chromatographic matrix according to the embodiment is preferably human IgG from the viewpoint of demand and importance as an antibody drug, though the antibody protein according to the embodiment is not limited thereto.

The cation exchange chromatographic matrix according to the embodiment is suitable for flow-through purification. The flow-through refers to a purification method that intends to allow the target physiologically active substance to pass through the matrix without being captured by the matrix. For example, in a case where a monomer of the antibody protein is a target and aggregates of the antibody protein are impurities, the antibody protein monomer passes through the matrix without adsorption while the antibody protein aggregates are adsorbed to the matrix. In this respect, the antibody protein monomer may be adsorbed to the matrix. However, the antibody protein monomer is purified by the more selective adsorption of the antibody protein aggregates to the matrix.

The shape of the base material comprised in the cation exchange matrix according to the embodiment is not particularly limited. The base material in a membrane form generally permits treatment at a high flow rate. Examples of the shape of the membrane include hollow fiber, flat membrane, nonwoven fabric, monolith, capillary, sintered body, disk, and cylindrical shapes. Furthermore, the material is not particularly limited. The base material is preferably made of a polyolefin polymer, polyamide (nylon), polyester, polyethersulfone, or cellulose, etc.

Examples of the polyolefin polymer include homopolymers of olefins such as ethylene, propylene, butylene and vinylidene fluoride, copolymers of two or more of the olefins, and copolymers of one or two or more of the olefins with a perhalogenated olefin. Examples of the perhalogenated olefin include tetrafluoroethylene and/or chlorotrifluoroethylene. Among them, polyethylene or polyvinylidene fluoride is preferred from the viewpoint of being excellent in mechanical strength and obtaining high absorption capacity for impurities such as protein. Examples of the polyamide include, but are not particularly limited to, nylon 6 (polycondensate of ε-caprolactam), nylon 11 (polycondensate of undecane lactam), nylon 12 (polycondensate of lauryllactam), nylon 66 (copolycondensate of hexamethylenediamine and adipic acid), nylon 610 (copolycondensate of hexamethylenediamine and adipic acid), nylon 6T (copolycondensate of hexamethylenediamine and terephthalic acid), nylon 9T (copolycondensate of nonanediamine and terephthalic acid), nylon M5T (copolycondensate of methylpentanediamine and terephthalic acid), nylon 621 (copolycondensate of caprolactam and lauryllactam), a copolycondensate of p-phenylenediamine and terephthalic acid, and a copolycondensate of m-phenylenediamine and isophthalic acid. Examples of the polyester include, but are not particularly limited to, polyethylene terephthalate, polytrimethylene terephthalate, polybutylene terephthalate, polyethylene naphthalate, and polybutylene naphthalate.

The base material has, for example, a plurality of pores. The pore size is not particularly limited. In a case where the base material is in a hollow fiber form, the pore size is, for example, 5 nm or larger and 1000 nm or smaller, preferably 10 nm or larger, more preferably 50 nm or larger, further preferably 100 nm or larger, particularly preferably 150 nm or larger or 400 nm or larger. Also, the pore size is preferably 900 nm or smaller, more preferably 800 nm or smaller, further preferably 700 nm or smaller, particularly preferably 650 nm or smaller, from the viewpoint of the membrane surface area of the base material. In a case where the pore size is 5 nm or larger, the antibody protein that can be separated tends to have a larger molecular weight. In a case where the pore size is 1000 nm or smaller, the base material in a membrane form tends to have a larger surface area and also have larger binding capacity for impurities.

In a case where the base material is in a flat membrane form or in a nonwoven fabric form, the preferred range of the pore size is widened in using the cation exchange chromatographic matrix because a matrix may be used, or such base materials may be layered for use. Hence, in a case where the base material is in a flat membrane form or in a nonwoven fabric form, the preferred range of the pore size is 10 nm or larger and 1 mm or smaller, preferably 100 nm or larger, more preferably 200 nm or larger, further preferably 300 nm or larger. Also, the pore size is preferably 500 um or smaller, more preferably 300 um or smaller, further preferably 100 um or smaller, from the viewpoint of the surface area.

The cation exchange chromatographic matrix according to the embodiment comprises a copolymer immobilized on the base material through a covalent bond by a graft polymerization method. Examples of the graft polymerization method include a radiation graft polymerization method and a surface living radical polymerization method.

In the case of immobilizing the copolymer onto the base material surface by the radiation graft polymerization method, any approach may be adopted for generating radicals in the base material. The irradiation of the base material with ionizing radiation is preferred because radicals are uniformly generated throughout the base material. γ ray, electron beam, β ray, and neutron ray, etc. can be used as the species of the ionizing radiation. Electron beam or γ ray is preferred for execution at an industrial scale. The ionizing radiation is obtained from a radioisotope such as cobalt 60, strontium 90, or cesium 137, or using X ray equipment, an electron beam accelerator or an ultraviolet irradiation apparatus, etc.

The irradiation dose of the ionizing radiation is preferably 1 kGy or larger and 1000 kGy or smaller, more preferably 2 kGy or larger and 500 kGy or smaller, further preferably 5 kGy or larger and 200 kGy or smaller. In a case where the irradiation dose is 1 kGy or larger, radicals tend to be easily generated uniformly. Also, the irradiation dose is preferably 1000 kGy or smaller from the viewpoint of the physical strength of the base material in a membrane form.

In general, graft polymerization methods based on irradiation with ionizing radiation are broadly classified into: a preirradiation method which involves generating radicals in the base material, and subsequently contacting the radicals with a reactive compound; and a simultaneous irradiation method which involves generating radicals in the base material with the base material in contact with a reactive compound. In the embodiment, any of the methods is applicable, and the preirradiation method, which is less likely to produce an oligomer, is preferred. In this context, the oligomer refers to a free oligomer. It is preferred the free oligomer should not be produced because the free oligomer is not incorporated into a graft chain.

In the embodiment, the solvent for use in the polymerization for the copolymer is not particularly limited as long as the solvent can uniformly dissolve a reactive compound. Examples of such a solvent include: alcohols such as methanol, ethanol, isopropanol, and t-butyl alcohol; ethers such as diethyl ether and tetrahydrofuran; ketones such as acetone and 2-butanone; water; and mixtures thereof.

One monomer unit of the copolymer immobilized on the base material in the cation exchange chromatographic matrix according to the embodiment has at least a sulfonic acid group.

The copolymer having cation exchange groups is immobilized on the base material by the graft polymerization method so that the cation exchange groups present in a graft chain are sterically arranged. Hence, the molecules to be adsorbed can be sterically adsorbed as compared with the case where cation exchange groups are distributed only on the base material surface. Accordingly, for antibody purification, antibody aggregates having a larger molecular weight than that of an antibody monomer are selectively adsorbed to the base material through binding at multiple points with the cation exchange groups on the graft chain. As a result, the antibody monomer can be obtained at a high purity.

Not only the removal of antibody aggregates but the removal of host cell-derived protein (HCP) and the like having a wide pI distribution is important for an antibody purification process. Therefore, it is preferred for flow-through purification using a cation exchange matrix that the purification can be performed even at low pH. Hence, the cation exchange chromatographic matrix according to the embodiment comprises a sulfonic acid group, which is a strong cation exchange group that is charged even at low pH and can adsorb impurities, as compared with a weak cation exchange group such as a carboxylic acid group.

In the cation exchange chromatographic matrix according to the embodiment, the copolymer has substantially no cross-linked structure from the viewpoint of selectivity for more strongly adsorbing antibody aggregates than an antibody monomer. In a case where the copolymer has substantially no cross-linked structure, the antibody aggregates can be sterically adsorbed to the base material because the molecular chain of the copolymer on the base material gets up in association with liquid injection.

In this context, the phrase "having substantially no cross-linked structure" also means that the copolymer, even if having a cross-linked structure, has a low degree of cross-linking that has no substantial influence on antibody aggregate adsorption capability. The cross-linked structure is formed within the copolymer or between adjacent copolymers if the copolymer comprises a monomer unit containing two or more polymerizable functional groups. In a case where the copolymer has substantially no cross-linked structure, the mass ratio of the monomer unit containing two or more polymerizable functional groups to the copolymer is, for example, 10% or less, 5% or less, 4% or less, 3% or less, 2% or less, 1% or less, 0.5% or less, or 0.1% or less, and a lower mass ratio is more preferred.

The cation exchange chromatographic matrix according to the embodiment comprises neither acrylamide nor an acrylamide derivative as a monomer unit, or comprises acrylamide or an acrylamide derivative as a monomer unit in a range which has no substantial influence.

A copolymer comprising acrylamide or an acrylamide derivative as a monomer unit has temperature responsiveness. Therefore, if the copolymer comprises at least any of acrylamide and an acrylamide derivative, impurity removal capability tends to be changed due to temperature during purification. By contrast, the cation exchange chromatographic matrix according to the embodiment comprises neither acrylamide nor an acrylamide derivative, or comprises acrylamide or an acrylamide derivative, if any, in a range which has no influence, for the reproducibility and stability of a purification step. The phrase "comprising in a range which has no influence" refers to comprising acrylamide and/or an acrylamide derivative at a mass ratio of, for example, 50% or less, 40% or less, 30% or less, 20% or less, 10% or less, 5% or less, 3% or less, 2% or less, or 1% or less in all monomer units of the copolymer.

The binding rate of the graft chain (graft rate) of the cation exchange chromatographic matrix according to the embodiment may differ in optimum value depending on the density of the base material. In a case where the base material is made of polyethylene, the graft rate is preferably 10% or more, more preferably 25% or more, further preferably 30% or more, particularly preferably 40% or more, 50% or more, 60% or more, or 70% or more, from the viewpoint of absorption capacity and steric adsorption. Also, the graft rate is preferably 200% or less, more preferably 150% or less, further preferably 120% or less, from the viewpoint of securing mechanically stable strength. The graft rate is represented by the following expression (1):

$$dg(\%) = (w_1 - w_0)/w_0 \times 100 \qquad (1)$$

In this context, $w_0$ is the mass of the base material (e.g., porous hollow fiber) before introduction of the graft chain, and $w_1$ is the mass of the base material after introduction of the graft chain. In the present disclosure, the graft rate is defined by change in mass between before and after graft polymerization without taking into consideration change in mass caused by functional group conversion after graft polymerization.

In a case where the base material is made of polyvinylidene fluoride, the graft rate suitable for polyvinylidene fluoride differs from that for polyethylene because the polyvinylidene fluoride has a higher density than that of the polyethylene. In a case where the base material is made of polyvinylidene fluoride, the graft rate is preferably 5% or more, more preferably 10% or more, from the viewpoint of absorption capacity. Also, the graft rate is preferably 100% or less, more preferably 80% or less, further preferably 70% or less, from the viewpoint of securing mechanically stable strength.

The ratio of the graft chain can also be represented as the mass of the graft chain per cation exchange chromatographic matrix volume (graft chain density). In this case, the graft chain density is preferably 0.03 g/mL or larger, more preferably 0.04 g/mL or larger, further preferably 0.05 g/mL or larger, particularly preferably 0.06 g/mL or larger, 0.07 g/mL or larger, 0.08 g/mL or larger, 0.09 g/mL or larger, 0.1 g/mL or larger, 0.11 g/mL or larger, or 0.12 g/mL or larger, from the viewpoint of absorption capacity, etc. The graft chain density is preferably 0.25 g/mL or smaller, more preferably 0.20 g/mL or smaller, further preferably 0.18 g/mL or smaller, from the viewpoint of mechanically stable strength. In the present disclosure, the values described above are calculated from the amount of the graft chain of the cation exchange matrix obtained as a final product, not in the course of manufacture. The graft chain density is represented by the following expression (2):

$$sg(g/mL) = (w_2 - w_0)/v_1 \qquad (2)$$

In this context, $w_2$ is the mass of the cation exchange chromatographic matrix obtained as the final product, and $v_1$ is the volume of the cation exchange chromatographic matrix obtained as the final product. As mentioned above, $w_1$ in the expression (1) is the mass of the base material immediately after graft polymerization and before subsequent functional group conversion.

The range of the density of the sulfonic acid group in the cation exchange chromatographic matrix according to the embodiment is higher than 30 mmol/L and 200 mmol/L or lower. The "density" is generally represented as the concentration in terms of the number of moles of the cation exchange group per L of the cation exchange chromatographic matrix. The density of the cation exchange group is higher than 30 mmol/L, preferably 35 mmol/L or higher, more preferably 40 mmol/L or higher, further preferably 50 mmol/L or higher, 60 mmol/L or higher, or 70 mmol/L or higher, from the viewpoint of absorption capacity. Also, the density of the cation exchange group is 200 mmol/L or lower, preferably 170 mmol/L or lower, more preferably 150 mmol/L or lower, because too high a cation exchange group density tends to deteriorate selectivity for antibody aggregates over an antibody monomer.

The cation exchange chromatographic matrix according to the embodiment may or may not contain a weak cation exchange group such as a carboxyl group, in addition to the sulfonic acid group. However, a cation exchanger containing a weak cation exchange group such as a carboxyl group tends to largely vary in state depending on the pH of an antibody solution. Therefore, it is preferred that the cation exchange chromatographic matrix according to the embodiment should be substantially free from a weak cation exchange group such as a carboxyl group. The phrase "substantially free from a weak cation exchange group" means that the carboxylic acid group density is lower than 15 mmol/L, lower than 10 mmol/L, or lower than 5 mmol/L, though depending on the quantitative ratio between the strong cation exchange group and the weak cation exchange group. In the case of containing a carboxyl group, it is preferred that the density of the sulfonic acid group should be higher than the density of the carboxyl group. The density of the carboxylic acid group is, for example, ½ or less, more preferably ⅓ or less, further preferably ¼ or less, still further preferably ⅕ or less, particularly preferably ⅙ or less, of the density of the sulfonic acid group. Within such a range, the reproducibility of purification results tends to be easily obtained without being influenced by minor change in pH of an antibody solution.

In the cation exchange chromatographic matrix according to the embodiment, the molar ratio of the monomer unit having a sulfonic acid group in the copolymer is preferably smaller than the molar ratio of a neutral monomer unit having no charge and is preferably ½ or less, more preferably ⅓ or less, further preferably ¼ or less, particularly preferably ⅕ or less, of the molar ratio of a neutral monomer unit having no charge, from the viewpoint of selective adsorbability for antibody aggregates over an antibody monomer. Likewise, the ratio of the mass of the monomer unit having a sulfonic acid group to the mass of the neutral monomer unit in the copolymer is preferably ½ or less, more preferably ⅓ or less, further preferably ¼ or less, particularly preferably ⅕ or less.

As for the feed composition of a reaction solution in the synthesis of the cation exchange chromatographic matrix according to the embodiment, the molar ratio of a monomer having a sulfonic acid group or a monomer having a sulfonic acid group-introducing precursor is preferably smaller than the molar ratio of a neutral monomer and is preferably ½ or less, more preferably ⅓ or less, further preferably ¼ or less, particularly preferably ⅕ or less, of the molar ratio of a neutral monomer, from the viewpoint of selective adsorbability for aggregates. Likewise, the ratio of the mass of the monomer having a sulfonic acid group or the monomer having a sulfonic acid group-introducing precursor to the mass of the neutral monomer is preferably ½ or less, more preferably ⅓ or less, further preferably ¼ or less, particularly preferably ⅕ or less.

Examples of the method for introducing the cation exchange group according to the embodiment include, but are not particularly limited to, a method which involves further using a monomer having a sulfonic acid group during graft polymerization, and a method which involves copolymerizing monomers further using a monomer having a "sulfonic acid group-introducing precursor", and then converting the sulfonic acid group-introducing precursor to a sulfonic acid group.

In this context, the "sulfonic acid group-introducing precursor" refers to a functional group capable of conferring a sulfonic acid group. Examples thereof include, but are not limited to, an epoxy group. The monomer having the "sulfonic acid group-introducing precursor" refers to a monomer having a functional group capable of conferring a sulfonic acid group. The "sulfonic acid group-introducing precursor" may include a "sulfonic acid group precursor". The "sulfonic acid group precursor" is, for example, a sulfonic acid group attached with a protective group. Examples of the monomer having the "sulfonic acid group precursor" include, but are not limited to, phenyl vinylsulfonate.

Examples of the monomer unit having a sulfonic acid group include (meth)acrylamidoalkylsulfonic acid, vinylsulfonic acid, acrylamido-t-butylsulfonic acid, and styrenesulfonic acid, which are constitutional units of polymers having sulfonic acid.

Examples of the monomer having a sulfonic acid group-introducing precursor include styrene and glycidyl methacrylate. Use of a strong cation exchange group-introducing precursor monomer, such as glycidyl methacrylate, which at least partially has a methacrylic acid derivative or an acrylic acid derivative can produce a sufficient polymerization rate even in the case of polymerizing the monomer having a strong cation exchange group by a surface living radical polymerization method.

In a case where the monomer having a sulfonic acid group-introducing precursor is glycidyl methacrylate, a portion or the whole of epoxy groups in the glycidyl methacrylate may be converted to a sulfonic acid group through reaction with sodium sulfite after the polymerization of the glycidyl methacrylate. The conversion of the epoxy group to a sulfonic acid group can elevate the cation exchange group density.

The neutral monomer unit in the copolymer according to the embodiment is not particularly limited as long as the neutral monomer unit comprises no acrylamide derivative as a monomer unit, or comprises an acrylamide derivative as a monomer unit in a range which has no substantial influence. The neutral monomer unit includes a hydrophilic monomer unit and a hydrophobic monomer unit, any of which may be contained in the copolymer.

In the cation exchange chromatographic matrix according to the embodiment, the ratio of the mass of the hydrophilic monomer unit to the total mass of the neutral monomer unit in the copolymer is preferably 50% or more for performing the steric adsorption of impurities such as antibody aggregates to the graft chain. The ratio is more preferably 60% or more, further preferably 70% or more, still further preferably 80% or more, or may be 100%. At a larger ratio of a hydrophilic monomer, the graft chain tends to get up in an aqueous solution and facilitate steric adsorption. The molar ratio of the hydrophilic monomer unit to the neutral monomer unit in the copolymer is preferably 50% or more, more preferably 60% or more, further preferably 70% or more, still further preferably 80% or more, or may be 100%.

As for the feed composition of a reaction solution in the synthesis of the cation exchange chromatographic matrix according to the embodiment, the ratio of the mass of a hydrophilic monomer to the total mass of a neutral monomer is preferably 50% or more from the viewpoint of steric adsorption. The ratio is more preferably 60% or more, further preferably 70% or more, still further preferably 80% or more, or may be 100%. The molar ratio of the hydrophilic monomer to the neutral monomer in the feed composition is preferably 50% or more, more preferably 60% or more, further preferably 70% or more, still further preferably 80% or more, or may be 100%.

Examples of such a hydrophilic monomer include (meth)acrylate compounds such as 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 4-hydroxybutyl acrylate, 4-hydroxybutyl methacrylate, 2-(dimethylamino)ethyl acrylate, and 2-(dimethylamino)ethyl methacrylate, and mixtures thereof. 2-Hydroxyethyl methacrylate and 2-hydroxypropyl methacrylate are preferred.

After the conversion of epoxy groups in glycidyl methacrylate to a sulfonic acid group as mentioned above, unreacted epoxy groups can be converted to diol by treatment with an acid. In this case, a monomer unit containing the diol converted from the epoxy groups is hydrophilic. Usually, all the unreacted epoxy groups are converted to diol through reaction at 80° C. for approximately 2 hours using 0.5 mol/L sulfuric acid.

The neutral monomer unit in the copolymer may or may not comprise a hydrophobic monomer unit. The hydrophobic monomer unit contained in the copolymer strengthens hydrophobic interaction with an antibody and may further improve impurity removal efficiency.

Examples of such a hydrophobic monomer unit include styrenes, alkylacrylamides, alkylmethacrylamides, alkyl acrylates, and alkyl methacrylates. Alkylacrylamides, alkylmethacrylamides, alkyl acrylates, and alkyl methacrylates are preferred from the viewpoint of mechanical strength. The alkyl group is a linear or branched alkyl group having 4 or more carbon atoms, which is capable of exerting substantially hydrophobic interaction with an antibody.

The purification method for obtaining a physiologically active substance with an improved purity according to the embodiment is a purification method for purifying a physiologically active substance from a mixed solution containing impurities and the physiologically active substance, comprising contacting the mixed solution with the cation exchange chromatographic matrix mentioned above. The recovery rate of the physiologically active substance by the purification method according to the embodiment is, for example, 80% or more. The recovery rate is calculated according to the following expression (3):

$$\text{Recovery rate} = \frac{(\text{Amount of the antibody recovered} \times \text{Monomer component purity after treatment})}{(\text{Antibody throughput} \times \text{Monomer component purity before treatment})} \quad (3)$$

A buffer solution (buffer) other than a strong acid and a strong alkali can be used as a mobile phase in chromatography for the flow-through purification according to the embodiment. No organic solvent is necessary therefor. Concrete examples of the buffer solution include a phosphate buffer solution, a Tris buffer solution, a citrate buffer solution, and an acetate buffer solution. The buffer solution is not particularly limited as long as the buffer solution is usually used. The buffer (buffer solution) concentration is 1 mmol/L or higher and 200 mmol/L or lower, preferably 2 mmol/L or higher and 100 mmol/L or lower, more preferably 5 mmol/L or higher and 70 mmol/L or lower, further preferably 10 mmol/L or higher and 50 mmol/L or lower, still further preferably 10 mmol/L or higher and 40 mmol/L or lower, particularly preferably 10 mmol/L or higher and 30 mmol/L or lower. In this context, the buffer concentration refers to the concentration of an active ingredient in the buffer. For example, the buffer concentration of an acetate buffer usually prepared from acetic acid and sodium acetate is the total concentration of acetic acid and sodium acetate. The buffer concentration of a Tris buffer refers to the concentration of trishydroxymethylaminoethane. As for a buffer described as an acetic acid-Tris buffer or the like, the buffer concentration is the concentration of the former ingredient and refers to the concentration of acetic acid for acetic acid-Tris and the concentration of Tris for Tris-acetic acid.

The buffer solution according to the embodiment may or may not contain an inorganic salt such as sodium chloride. The concentration of the inorganic salt is 0 mmol/L or higher and 100 mmol/L or lower, preferably 0 mmol/L or higher and 90 mmol/L or lower, more preferably 0 mmol/L or higher and 80 mmol/L or lower, further preferably 0 mmol/L or higher and 70 mmol/L or lower, still further preferably 0 mmol/L or higher and 60 mmol/L or lower, still further preferably 0 mmol/L or higher and 50 mmol/L or lower, still further preferably 0 mmol/L or higher and 40 mmol/L or lower, still further preferably 0 mmol/L or higher and 30 mmol/L or lower. However, the preferred concentration of the inorganic salt in the buffer solution may vary depending on the amplitude of the isoelectric point of the protein to be treated, and the pH combination of buffer solutions.

If the buffer solution according to the embodiment is indicated by an index electrical conductivity, the electrical conductivity is 0.5 mS/cm or higher and 20 mS/cm or lower, preferably 0.5 mS/cm or higher and 15 mS/cm or lower, more preferably 0.5 mS/cm or higher and 10 mS/cm or lower, further preferably 0.8 mS/cm or higher and 8 ms/cm or lower, still further preferably 0.5 mS/cm or higher and 5 mS/cm or lower, still further preferably 0.5 mS/cm or higher and 4 mS/or lower, still further preferably 0.5 mS/cm or higher and 3 mS/cm or lower. However, the preferred electrical conductivity of the buffer solution may vary depending on the amplitude of the isoelectric point of the protein to be treated, and the pH combination of buffer solutions.

The pH of the buffer solution is preferably 4.0 or higher and 10.0 or lower, more preferably 4.5 or higher and 9.5 or lower, particularly preferably 5.0 or higher and 9.0 or lower. However, the preferred pH of the buffer solution may vary depending on the amplitude of the isoelectric point of the protein to be treated, and the inorganic salt concentration combination of the buffer solution.

The flow rate in loading an antibody solution in the flow-through purification using cation exchange chromatography according to the embodiment is preferably one or more times, more preferably two or more times, further preferably three or more times or four or more times, particularly preferably five or more times the membrane volume per minute from the viewpoint of purification efficiency. Also, the flow rate is preferably 30 or less times, more preferably 20 or less times, further preferably 15 or less times, particularly preferably 10 or less times the membrane volume from the viewpoint of a contact time with impurities.

The amount of the antibody protein (including the monomer and the aggregates) loaded in the flow-through purification using cation exchange chromatography according to the embodiment is not particularly limited and is 100 mg or more per mL of the matrix, preferably 500 mg or more, more preferably 700 mg or more, further preferably 800 mg or more, still further preferably 900 mg or more, particularly preferably 1 g or more, per mL of the matrix from the viewpoint of efficient purification.

The concentration of a solution of the antibody protein including the monomer and the aggregates in the flow-through purification using cation exchange chromatography according to the embodiment is, for example, 2.0 mg/mL or higher, preferably 3.0 mg/mL or higher, more preferably 4.0 mg/mL or higher, further preferably 4.5 mg/mL or higher, still further preferably 5.0 mg/mL or higher, particularly preferably 5.5 mg/mL or higher. Alternatively, 6.0 mg/mL or higher, 7.0 mg/mL or higher, or the like is also preferred. The antibody protein solution having a higher concentration tends to produce higher purification efficiency.

According to the flow-through purification using cation exchange chromatography according to the embodiment, the ratio of the aggregates of the antibody protein is reduced by 50% or more and reduced more preferably by 60% or more, further preferably by 70% or more, particularly preferably by 80% or more. The reduction rate of the ratio of the aggregates of the antibody protein is a value indicated by percentage obtained by subtracting the content ratios of aggregate components (1) and (2) after treatment from the content ratios of the aggregate components (1) and (2) before treatment in FIG. 2 (enlarged view of a portion of a chromatographic chart shown in FIG. 1), and dividing the difference by the content ratios of the aggregate components (1) and (2) before treatment. The respective content ratios of the aggregate components (1) and (2) are calculated from a peak area in the chromatographic chart as illustrated in FIG. 2.

The purification step by cation exchange chromatography according to the embodiment can be combined with a purification step by anion exchange chromatography to further improve the purity of a purified product. Specifically, in the case of removing impurities having lower pI than that of the target substance in the flow-through purification according to the embodiment, purification using an anion exchange chromatographic matrix may be combined therewith. The combination of the purification step using the cation exchange chromatographic matrix according to the embodiment with a purification step using an anion exchange chromatographic matrix can achieve efficient purification while maintaining removability of impurities having higher pI than that of the target substance.

Examples of the impurities having lower pI than that of the target substance include, but are not particularly limited to, host cell-derived protein (HCP), DNA, and protein A which is an impurity derived from an affinity chromatography step.

The purification step using an anion exchange chromatographic matrix may be performed before or after the purification step using the cation exchange chromatographic matrix.

The anion exchange chromatographic matrix is not particularly limited. The anion exchange chromatographic matrix in a membrane form is capable of treatment at a high flow rate and permits construction of a more efficient purification step. The anion exchange chromatographic matrix may have a structure having a graft polymer chain on a base material. The structure having a graft polymer on a base material can sterically adsorb impurities and can therefore produce higher impurity removability.

The purification method using the anion exchange chromatographic matrix is not particularly limited. Flow-through purification achieves more efficient purification.

The amount of the antibody protein (including the monomer and the aggregates) loaded in the anion exchange chromatography step is not particularly limited as long as impurities can be removed. The amount of the antibody protein loaded is preferably 0.2 g or more, more preferably 0.5 g or more, further preferably 1.0 g or more, still further preferably 2.0 g or more, particularly preferably 4.0 g or more, per mL of the matrix from the viewpoint of efficient purification.

Buffer replacement may or may not be performed between the purification step using the cation exchange chromatographic matrix and the purification step using the anion exchange chromatographic matrix. More efficient purification can be performed without buffer replacement.

The purification step using the cation exchange chromatographic matrix and the purification step using the anion exchange chromatographic matrix may be continuously performed, or after the completion of a preceding step, the purified product may be temporarily stored in a tank and subjected to a next step.

The pH adjustment of the solution may be performed between the purification step using the cation exchange chromatographic matrix and the purification step using the anion exchange chromatographic matrix. The pH adjustment further enhances the removability of impurities having pI around the treatment pH of the preceding step. Specifically, in the case of first performing purification using the cation exchange chromatographic matrix, the pH of the solution is elevated by the addition of a base to the solution before purification using the anion exchange chromatographic matrix. As a result, the impurities are negatively charged and can therefore be more easily removed by anion exchange chromatography. Alternatively, in the case of first performing purification using the anion exchange chromatographic matrix, the pH of the solution is lowered by the addition of an acid to the solution before purification using the cation exchange chromatographic matrix. As a result, the impurities are positively charged. Therefore, the pI range of the impurities that can be removed by cation exchange chromatography is widened so that the impurities can be more easily removed. The pH value to be changed is not particularly limited as long as impurity removability is improved. The pH can be arbitrarily changed according to the target impurities. Examples of the value of the amount of change in pH include 0.01, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0. Any of these values may be used, or a value between the values may be used. The amount of change in pH is not particularly limited as long as the impurities can be removed. Preferably, change in pH by 0.1 or more particularly improves impurity removability.

As in pH, the electrical conductivity adjustment of the solution may be performed between the purification step using the cation exchange chromatographic matrix and the purification step using the anion exchange chromatographic matrix. The value of the electrical conductivity to be changed is not particularly limited as long as impurity removability is improved. The electrical conductivity can be arbitrarily changed according to the target impurities. Examples of the value of the amount of change in electrical conductivity include 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, and 5.0 mS/cm. Any of these values may be used, or a value between the values may be used.

In general antibody purification, purification in an ion exchange chromatography step is performed after purification by affinity chromatography. An affinity chromatography step may be performed before the purification step by cation exchange chromatography according to the embodiment and the anion exchange chromatography step. The target can be obtained with a higher purity by performing the flow-through purification by cation exchange chromatography and the anion exchange chromatography step after the affinity chromatography step. The affinity chromatographic matrix refers to a matrix carrying, for example, protein A or protein G. The affinity chromatography step is carried out, for example, in a bind and elute mode.

Efficient purification is achieved by performing the flow-through purification by cation exchange chromatography and flow-through purification by anion exchange chromatography without buffer replacement of an antibody-containing eluate after the affinity chromatography step. Such an eluate is a buffer containing a monovalent acid as a main component. Examples thereof include an acetate buffer.

In a general anion exchange chromatography step, use of an elution buffer containing a polyvalent acid as a main component tends to decrease the amount of adsorption and reduce impurity removal capability. Therefore, in the case of using an elution buffer containing a polyvalent acid as a main component in an affinity chromatography step, it is preferred to replace the buffer before anion exchange chromatography. Thus, elution using the elution buffer containing a monovalent acid as a main component in the affinity chromatography step eliminates the need of buffer replacement and achieves more convenient purification in the cation exchange chromatography step and the anion exchange chromatography step.

The elution buffer containing a monovalent acid as a main component is not particularly limited as long as the elution buffer is capable of elution in the affinity chromatography step and permits removal of impurities in the subsequent ion exchange chromatography step. Acetic acid is preferred. In a case where the elution buffer is acetic acid, the pH can be easily adjusted to pH required for the subsequent step even without buffer replacement, etc.

The elution buffer for use in elution in the affinity chromatography step has an electrical conductivity of, but not limited to, preferably 10.0 mS/cm or lower, more preferably 7.0 mS/cm or lower, further preferably 5.0 mS/cm or lower, still further preferably 3.0 mS/cm or lower, particularly preferably 2.5 mS/cm or lower, from the viewpoint of the impurity removability of the subsequent flow-through purification by cation exchange chromatography. The electrical conductivity is preferably 100 mmol/L or lower, more preferably 50 mmol/L or lower, further preferably 40 mmol/L or lower, still further preferably 30 mmol/L or lower, particularly preferably 25 mmol/L or lower, from the viewpoint of a buffer concentration.

For maintaining the low electrical conductivity of an elution pool into which the physiologically active substance is eluted, it is preferred to wash the matrix with a buffer solution having a low electrical conductivity immediately before elution in the affinity chromatography step. The buffer solution can have sufficiently high pH and a sufficiently low electrical conductivity so as not to elute the physiologically active substance. The electrical conductivity of the elution pool is kept low and can thereby be easily adjusted to an electrical conductivity required for the subsequent step. Furthermore, the denaturation of the physiologically active substance and the formation of aggregates can be prevented.

Such pH is preferably 5.0 or higher, more preferably 6.0 or higher, further preferably 7.0 or higher. The electrical conductivity is preferably 10.0 mS/cm or lower, more preferably 7.0 mS/cm or lower, further preferably 5.0 mS/cm or lower, particularly preferably 3.0 mS/cm or lower.

After the elution in the affinity chromatography step, a virus that may be contained in the eluate may be inactivated by the exposure of the virus to acidic (low pH) conditions for a given time. For the virus inactivation, the pH is preferably 4.0 or lower, more preferably 3.8 or lower, further preferably 3.6 or lower, still further preferably 3.5 or lower, particularly preferably 3.4 or lower.

The acid for adjusting the eluate to low pH is not particularly limited and may be a strong acid or may be a weak acid. However, the acid is desirably a strong acid from the viewpoint that the amount of the acid added can be small and from the viewpoint of the convenience of subsequent neutralization operation. Examples of such a strong acid include hydrochloric acid.

The electrical conductivity of the mixed solution containing the physiologically active substance according to the embodiment may be constantly 10 mS/cm or lower in a series of steps including the affinity chromatography step, the virus inactivation by low-pH treatment, the cation exchange chromatography step, and the anion exchange chromatography step. In a case where the electrical conductivity is constantly 10 ms/cm or lower, the impurities tend to be easily removed. The electrical conductivity may be 9.0 or lower and is preferably 8.0 or lower, more preferably 7.0 or lower, further preferably 6.0 or lower, still further preferably 5.0 or lower, still further preferably 4.0 or lower, particularly preferably 3.0 or lower.

EXAMPLES

Hereinafter, the embodiment will be described in more detail with reference to Examples. However, the embodiment is not limited by these examples by any means.

Example 1

In Example 1, a cation exchange membrane in a hollow fiber form was prepared by the radiation graft polymerization method.

1) Preparation of Cation Exchange Membrane 7.07 g of 2-hydroxyethyl methacrylate and 0.79 g of glycidyl methacrylate were dissolved in 113 mL of methanol, and the solution was bubbled with nitrogen for 30 minutes and used as a reaction solution. 3.03 g (15 cm, 15 fibers) of polyethylene porous hollow fibers having an outside diameter of 3.0 mm, an inside diameter of 2.0 mm, and an average pore size of 0.25 um was placed in a closed container, and air in the container was replaced with nitrogen. Then, the container was irradiated with 25 kGy of γ ray while cooled on dry ice from the outside to generate radicals. The polyethylene porous hollow fibers having the obtained radicals were transferred to a glass container, and oxygen in the reaction tube was removed by reduction in pressure to 200 Pa or lower. 55 mL of the reaction solution adjusted to 40° C. was introduced thereto, and the container was left standing for 16 hours. Then, the hollow fibers were washed with methanol and vacuum-dried in a vacuum dryer to obtain 6.13 g of a hollow fiber membrane having a graft rate of 103%.

The hollow fibers with the graft chain introduced by the radiation graft polymerization method were added into 160 g of a mixed aqueous solution of sodium sulfite and isopropyl alcohol (sodium sulfite/isopropyl alcohol/pure water=10/15/75 wt %) and reacted at 80° C. for 20 hours to convert epoxy groups in the graft chain to sulfonic acid groups. The hollow fibers thus reacted were washed with pure water. Then, the hollow fibers were added into 0.5 mol/L sulfuric acid and reacted at 80° C. for 2 hours to convert epoxy groups remaining in the graft chain to diol groups. The hollow fibers were washed with water and methanol and then vacuum-dried to obtain 6.29 g of cation exchange membrane 1.

One (0.419 g) of the hollow fibers was wetted with ethanol and, after replacement with water, added into a graduated cylinder containing water. As a result of measuring the volume on the basis of increment in volume, the volume was 1.4 mL. Since the mass of the base material membrane was 0.202 g, the graft chain had a mass of 0.217 g and a density of 0.156 g/mL. After removal of water, 10 mL of a 0.1 mol/L aqueous sodium hydroxide solution was added to the membrane. The membrane was left for 1 hour. Then, the aqueous sodium hydroxide solution was taken out thereof, and 10 mL of pure water was added to the membrane. The membrane was further left for 1 hour. Then, pure water was recovered to recover sodium hydroxide remaining in the membrane. The recovered sodium hydroxide solutions were combined and titrated with 0.1 mol/L hydrochloric acid. As a result, 8.88 mL was required. Since 10.05 mL was required for the titration of a blank (hollow fibers having no ion exchange group), the amount of the sulfonic acid group reacted with sodium hydroxide, in the cation exchange membrane was 140 umol (0.000140 mol). This value was divided by the measured volume, and the calculated density of the sulfonic acid group was 100 mmol/L. The obtained cation exchange membrane 1 was prepared into a module (membrane volume: 0.30 mL) to obtain cation exchange membrane 1 according to Example 1.

The mass of the monomer unit having a sulfonic acid group can be determined from the amount of the sulfonic acid group. Since the molecular weight of the glycidyl methacrylate after conversion to sulfonic acid groups was 224.23, the mass of the monomer unit having a sulfonic acid group was 0.0314 g. The mass of the graft chain per hollow fiber was 0.217 g from the mass of the porous hollow fibers before and after reaction. Thus, the mass of the neutral monomer unit was 0.1856 g from the mass of the graft chain per hollow fiber and the mass of the monomer unit having a sulfonic acid group. Accordingly, the mass of the monomer unit having a sulfonic acid group was calculated to be 1/5.91 of the mass of the neutral monomer unit.

2) Preparation of Cell Culture Solution

A culture solution supernatant containing 0.151 g/L human monoclonal antibody expressed from CHO cells CRL12445 (hereinafter, referred to as "CRL12445 antibody") was prepared as an antibody protein. A culture solution containing CRL12445 antibody-producing cells was filtered through a filtration membrane (manufactured by Asahi Kasei Medical Co., Ltd., trade name: BioOptimal® MF-SL) to obtain an antibody solution (culture supernatant) containing impurities and the antibody.

3) Purification of Antibody Protein with Affinity Column

The antibody solution was added to a protein A column (column packed with MabSelect Sure manufactured by GE Healthcare Bio-Sciences Corp.) equilibrated with a phosphate buffer solution (20 mmol/L sodium phosphate+150 mmol/L NaCl (pH 8.0)) to adsorb the antibody protein to protein A. Next, the column was washed by the injection of a phosphate buffer solution (20 mmol/L sodium phosphate+ 150 mmol/L NaCl (pH 8.0)). Then, the antibody protein was eluted from the protein A column by the injection of an elution buffer solution (100 mmol/L sodium citrate (pH 3.6)) to the column to recover an antibody solution containing impurities in an amount reduced to some extent.

4) Preparation of Aggregate

A portion of the obtained antibody solution was adjusted to pH 2.5 by the addition of hydrochloric acid and left for 1 hour. Then, the solution was neutralized using an aqueous sodium hydroxide solution to prepare an antibody solution containing a large amount of antibody aggregates.

5) Preparation of Antibody Solution Containing Aggregate

The antibody solution obtained from the protein A column was buffer-replaced with a 15 mmol/acetate buffer solution (pH 5.0). The antibody solution containing a large amount of aggregates was buffer-replaced with a 15 mmol/L acetate buffer solution (pH 5.0). These solutions were mixed at an arbitrary ratio to prepare an antibody solution containing aggregates.

6) Measurement of Amount of Aggregate

The obtained antibody solution was assayed using a size exclusion chromatography (SEC) apparatus under the following conditions.

Column: ACQUITY YPLC BEH200 SEC 1.7 um (manufactured by Waters Corp.)

Column temperature: 30° C.

System: ACQUITY UPLC H CLASS (manufactured by Waters Corp.)

Mobile phase: 0.1 mol/L disodium hydrogen phosphate+ 0.2 mol/L aqueous L(+)-arginine solution (adjusted to pH 6.7 with hydrochloric acid)

Figure 2:
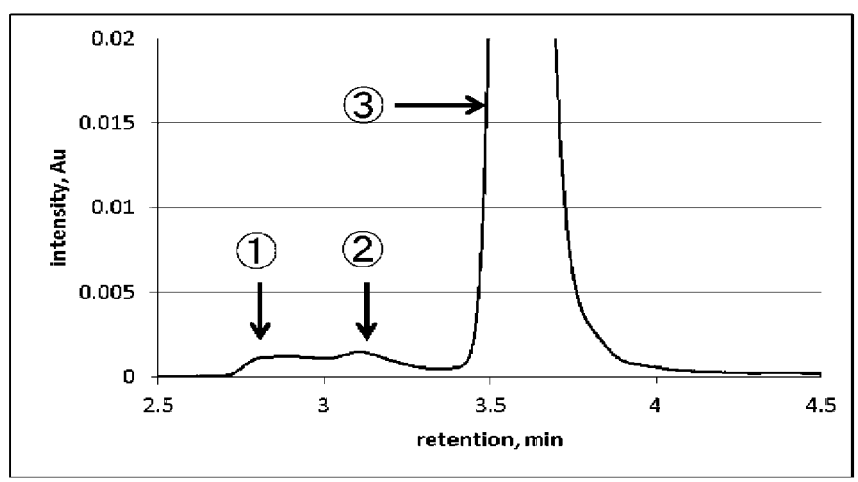
FIG. 2 is an enlarged view of the chromatographic chart of FIG. 1.

As a result, the chromatographic chart illustrated in FIG. 1 was obtained. An enlarged view thereof is shown in FIG. 2. The peaks that appeared at (1) and (2) in FIG. 2 are derived from the antibody aggregates, and the peak that appeared at (3) is derived from the monomer. The ratio of the aggregate (1) calculated from the peak area in the chromatographic chart was 2.35%, the ratio of the aggregate (2) was 1.92%, and the ratio of the monomer was 95.73%. In Examples and Comparative Examples below, the peak of the aggregate appearing first is referred to as an aggregate (1), and the peak of the aggregate appearing in the next place is referred to as an aggregate (2).

7) Removal of Aggregate

The antibody solution containing the aggregate components (impurities) and the monomer component (target physiologically active substance) of the antibody protein was contacted with the cation exchange membrane 1. The amount of the antibody solution added was 50 mL (concentration: 5.36 mg/mL, total amount of the antibody protein: 268 mg), and the flow rate was 1.5 mL/min. After the injection of the antibody solution, the cation exchange membrane 1 was washed using 10 mL of a 15 mmol/L acetate buffer solution (pH 5.0) at a flow rate of 1.5 mL/min. 60 mL of a solution was recovered by the flow-through step and the washing step. As a result of analyzing the recovered solution by size exclusion chromatography (SEC), the content of the aggregate components was decreased. The results are shown in FIG. 3.

Example 2

In Example 2, the same operation as in Example 1 was performed except that a different buffer solution (15 mmol/L acetate buffer solution of pH 5.0 containing 30 mmol/L sodium chloride) was used in the antibody solution and the washing step. The amount of the antibody solution treated was 50 mL, and the concentration thereof was 5.56 mg/mL. The results are shown in FIG. 3.

Example 3

In Example 3, the same operation as in Example 2 was performed except that a different buffer solution (15 mmol/L acetate buffer solution of pH 5.0 containing 50 mmol/L sodium chloride) was used in the antibody solution and the washing step. The amount of the antibody solution treated was 40 mL, and the concentration thereof was 5.56 mg/mL. The results are shown in FIG. 3.

Example 4

In Example 4, the same operation as in Example 1 was performed except that a different buffer solution (15 mmol/L acetate buffer solution of pH 6.0) was used in the antibody solution and the washing step. The amount of the antibody solution treated was 60 mL, and the concentration thereof was 5.70 mg/mL. The results are shown in FIG. 3.

Example 5

In Example 5, the same operation as in Example 1 was performed except that a different buffer solution (15 mmol/L acetate buffer solution of pH 6.0 containing 10 mmol/L sodium chloride) was used in the antibody solution and the washing step. The amount of the antibody solution treated was 60 mL, and the concentration thereof was 5.71 mg/mL. The results are shown in FIG. 3.

Example 6

In Example 6, the same operation as in Example 1 was performed except that a different buffer solution (15 mmol/L acetate buffer solution of pH 6.0 containing 30 mmol/L sodium chloride) was used in the antibody solution and the washing step. The amount of the antibody solution treated was 60 mL, and the concentration thereof was 5.96 mg/mL. The results are shown in FIG. 3.

Example 7

In Example 7, the same operation as in Example 1 was performed except that a different buffer solution (15 mmol/L acetate buffer solution of pH 6.0 containing 50 mmol/L sodium chloride) was used in the antibody solution and the washing step. The amount of the antibody solution treated was 60 mL, and the concentration thereof was 5.91 mg/mL. The results are shown in FIG. 3.

Example 8

In Example 8, the same operation as in Example 1 was performed except that a different buffer solution (15 mmol/L Tris buffer solution of pH 7.0) was used in the antibody solution and the washing step. The amount of the antibody solution treated was 60 mL, and the concentration thereof was 5.69 mg/mL. The results are shown in FIG. 3.

Example 9

Example 9 shows an example in which 2 g or more of the antibody including the aggregates was treated per mL of the membrane volume. The same operation as in Example 8 was performed except that the amount of the antibody solution treated was 120 mL, and the concentration of the antibody solution was 5.89. The results are shown in FIG. 3.

Example 10

In Example 10, the same operation as in Example 1 was performed except that a different buffer solution (15 mmol/L acetate buffer solution of pH 7.0 containing 10 mmol/L sodium chloride) was used in the antibody solution and the washing step. The amount of the antibody solution treated was 60 mL, and the concentration thereof was 5.57 mg/mL. The results are shown in FIG. 3.

Example 11

In Example 11, the same operation as in Example 1 was performed except that a different buffer solution (15 mmol/L acetate buffer solution of pH 7.0 containing 30 mmol/L sodium chloride) was used in the antibody solution and the washing step. The amount of the antibody solution treated was 60 mL, and the concentration thereof was 5.67 mg/mL. The results are shown in FIG. 3.

Example 12

In Example 12, the same operation as in Example 1 was performed except that a different buffer solution (15 mmol/L Tris buffer solution of pH 8.0) was used in the antibody solution and the washing step. The amount of the antibody solution treated was 50 mL, and the concentration thereof was 5.53 mg/mL. The results are shown in FIG. 3.

Example 13

In Example 13, the same operation as in Example 1 was performed except that a different buffer solution (15 mmol/L Tris buffer solution of pH 9.0) was used in the antibody solution and the washing step. The amount of the antibody solution treated was 50 mL, and the concentration thereof was 5.44 mg/mL. The results are shown in FIG. 3.

Example 14

In Example 14, a culture solution supernatant containing 0.172 g/L AE6F4 antibody (human monoclonal antibody) was prepared as an antibody protein. AE6F4-producing cells were kindly provided by associate professor Yoshinori Katakura at Faculty of Agriculture, Kyushu University. The AE6F4 antibody-producing cells were cultured with reference to the literature (Proceedings of The Society for Biotechnology, Japan, Annual Meeting, 1994, Vol. 65, p. 65). The culture solution containing the AE6F4 antibody-producing cells was filtered through a filtration membrane (manufactured by Asahi Kasei Medical Co., Ltd., trade name: BioOptimal® MF-SL) to obtain an antibody solution (culture supernatant) containing impurities and the antibody.

The same operation as in Example 1 was performed except for the procedures described above. The amount of the antibody solution treated was 30 mL, and the concentration thereof was 5.92 mg/mL. The results are shown in FIG. 3.

Example 15

In Example 15, the same operation as in Example 14 was performed except that a different buffer solution (15 mmol/L citrate buffer solution of pH 5.0 containing 30 mmol/L sodium chloride) was used in the antibody solution and the washing step. The amount of the antibody solution treated was 40 mL, and the concentration thereof was 5.66 mg/mL. The results are shown in FIG. 3.

Example 16

In Example 16, the same operation as in Example 14 was performed except that a different buffer solution (15 mmol/L acetate buffer solution of pH 6.0) was used in the antibody solution and the washing step. The amount of the antibody solution treated was 30 mL, and the concentration thereof was 5.50 mg/mL. The results are shown in FIG. 3.

Example 17

In Example 17, the same operation as in Example 14 was performed except that a different buffer solution (15 mmol/L Tris buffer solution of pH 7.0) was used in the antibody solution and the washing step. The amount of the antibody solution treated was 40 mL, and the concentration thereof was 5.67 mg/mL. The results are shown in FIG. 3.

Comparative Example 1

In Comparative Example 1, cation exchange membrane 2 described below was used. The cation exchange membrane 2 was prepared as follows: 3.08 g of 2-hydroxyethyl methacrylate, 1.54 g of butyl methacrylate, and 0.57 g of methacrylic acid were dissolved in 240 mL of an aqueous solution containing 50% by volume of t-butyl alcohol, and the solution was bubbled with nitrogen for 30 minutes and used as a reaction solution. 3.00 g (15 cm, 15 fibers) of polyethylene porous hollow fibers having an outside diameter of 3.0 mm, an inside diameter of 2.0 mm, and an average pore size of 0.25 um was placed in a closed container, and air in the container was replaced with nitrogen. Then, the container was irradiated with 25 kGy of γ ray while cooled on dry ice from the outside to generate radicals. The polyethylene porous hollow fibers having the obtained radicals were transferred to a glass container, and oxygen in the reaction tube was removed by reduction in pressure to 200 Pa or lower. 140 mL of the reaction solution adjusted to 40° C. was introduced thereto, and the container was left standing for 16 hours. Then, the hollow fibers were washed with methanol and vacuum-dried in a vacuum dryer to obtain 5.31 g of a cation exchange membrane having a graft rate of 77%. The density of a weak cation exchange group carboxylic acid was 175 mmol/L by the same assay as in Example 1. This cation exchange membrane was prepared into a module (membrane volume: 0.25 mL) to obtain cation exchange membrane 2 according to Comparative Example 1.

Comparative Example 1 was carried out in the same way as in Example 1 except that the cation exchange membrane 2 was used. The results are shown in FIG. 3.

Comparative Example 2

In Comparative Example 2, the same operation as in Comparative Example 1 was performed except that a different buffer solution (15 mmol/L acetate buffer solution of pH 6.0) was used in the antibody solution and the washing step. The results are shown in FIG. 3.

Comparative Example 3

In Comparative Example 3, cation exchange membrane 3 described below was used. 7.72 g of 2-hydroxyethyl methacrylate and 0.13 g of glycidyl methacrylate were dissolved in 113 mL of methanol, and the solution was bubbled with nitrogen for 30 minutes and used as a reaction solution. 3.03 g (15 cm, 15 fibers) of polyethylene porous hollow fibers having an outside diameter of 3.0 mm, an inside diameter of 2.0 mm, and an average pore size of 0.25 um was placed in a closed container, and air in the container was replaced with nitrogen. Then, the container was irradiated with 25 kGy of γ ray while cooled on dry ice from the outside to generate radicals. The polyethylene porous hollow fibers having the obtained radicals were transferred to a glass container, and oxygen in the reaction tube was removed by reduction in pressure to 200 Pa or lower. 55 mL of the reaction solution adjusted to 40° C. was introduced thereto, and the container was left standing for 16 hours. Then, the hollow fibers were washed with methanol and vacuum-dried in a vacuum dryer to obtain 6.09 g of a hollow fiber membrane having a graft rate of 101%. Then, sulfonic acid groups were introduced in the same way as in Example 1 to obtain cation exchange membrane 8. The sulfonic acid group density was 22 mmol/L.

Aggregate removal was evaluated in the same way as in Example 1 except that the cation exchange membrane 3 was used. The results are shown in FIG. 3.

Comparative Example 4

In Comparative Example 4, cation exchange membrane 4 given below was used in which the total density of a strong cation exchange group and a weak cation exchange group was higher than 30 mmol/L, though the main component was composed mainly of the weak cation exchange group. The cation exchange membrane 4 was synthesized as follows: 3.09 g of N-isopropylacrylamide, 1.29 g of butyl methacrylate, 0.51 g of glycidyl methacrylate, and 0.26 g of t-butyl methacrylate were dissolved in 240 mL of an aqueous solution containing 50% by volume of t-butyl alcohol, and the solution was bubbled with nitrogen for 30 minutes and used as a reaction solution. 3.00 g (15 cm, 15 fibers) of polyethylene porous hollow fibers having an outside diameter of 3.0 mm, an inside diameter of 2.0 mm, and an average pore size of 0.25 um was placed in a closed container, and air in the container was replaced with nitrogen. Then, the container was irradiated with 200 kGy of γ ray while cooled on dry ice from the outside to generate radicals. The polyethylene porous hollow fibers having the obtained radicals were transferred to a glass container, and oxygen in the reaction tube was removed by reduction in pressure to 200 Pa or lower. 140 mL of the reaction solution adjusted to 40° C. was introduced thereto, and the container was left standing for 16 hours. Then, the hollow fibers were washed with methanol and vacuum-dried in a vacuum dryer to obtain 5.12 g of a cation exchange membrane precursor having a graft rate of 71%.

The hollow fibers with the graft chain introduced by the radiation graft polymerization method were added into 200 g of a mixed aqueous solution of sodium sulfite and IPA (sodium sulfite/IPA/pure water=10/15/75 wt %) and reacted at 80° C. for 24 hours to convert epoxy groups in the graft chain to sulfonic acid groups. The hollow fibers thus reacted were washed with pure water. Then, the hollow fibers were added into 0.5 mol/L sulfuric acid and reacted at 80° C. for 2 hours to convert epoxy groups remaining in the graft chain to diol groups. The hollow fibers were further reacted with 4 mL of methanesulfonic acid in 140 mL of chloroform, and the t-butyl group was deprotected and converted to a carboxyl group. As a result of measuring the total amount of the cation exchange groups and the membrane volume in the same way as in Example 1, they were 49 umol and 1.0 mL, respectively. Accordingly, the total cation exchange group density was 49 mmol/L.

The sulfonic acid group density was determined by the following method: all sulfonic acids were hydrogenated by dipping in 1 mol/L hydrochloric acid for 1 hour. The membrane was washed with pure water to remove hydrochloric acid. Then, 10 mL of a 1 mol/L aqueous sodium chloride solution was added thereto to elute hydrogen chloride. The membrane was left for 1 hour, and an aqueous sodium chloride solution containing hydrogen chloride was then recovered. Further, 10 mL of a 1 mol/L aqueous sodium chloride solution was added to the membrane, which was then left for 1 hour, followed by recovery to recover hydrogen chloride remaining in the membrane. The recovered products were combined and titrated using a 0.01 mol/L aqueous sodium hydroxide solution. As a result, 2.09 mL was required for neutralization. Since 0.29 mL was required for a blank, the membrane was found to have 18 mmol/L sulfonic acid groups. The membrane had 31 mmol/L carboxyl groups, which can be determined by subtracting the sulfonic acid group density from the total cation exchange group density.

Aggregate removal was evaluated in the same way as in Example 1 except that the cation exchange membrane 4 was used. The results are shown in FIG. 3.

Example 18

In Example 18, cation exchange membranes 5 to 13 differing in sulfonic acid group density were prepared under the same conditions as in Example 1 except that the monomer feed composition shown in FIG. 4 was used. FIG. 4 also shows the graft rate after synthesis, the sulfonic acid group density, the mass of the monomer unit having a sulfonic acid group/the mass of the monomer unit having no charge, and the graft chain density. The membrane volume was increased due to swelling with increase in graft rate. Therefore, a higher graft rate does not always mean a higher graft chain density.

Example 19

In Example 19, the cation exchange membranes 5 to 13 prepared in Example 18 were used. The same operation as in Example 1 was performed using an antibody solution of pH 5.0 for the cation exchange membranes 5 to 8. The same operation as in Example 4 was performed using an antibody solution of pH 6.0 for the cation exchange membranes 9 to 13. The results are shown in FIG. 5.

Example 20

In Example 20, cation exchange membrane 14 given below was synthesized, and aggregate removal was evaluated using the AE6F4 antibody in the same way as in Example 17 except that the cation exchange membrane 14 was used. For the preparation of the cation exchange membrane 14, 10.9 g of 2-hydroxypropyl methacrylate and 0.87 g of glycidyl methacrylate were dissolved in 109 mL of methanol, and the solution was bubbled with nitrogen for 30 minutes and used as a reaction solution. 3.02 g (15 cm, 15 fibers) of polyethylene porous hollow fibers having an outside diameter of 3.0 mm, an inside diameter of 2.0 mm, and an average pore size of 0.25 um was placed in a closed container, and air in the container was replaced with nitrogen. Then, the container was irradiated with 25 kGy of γ ray while cooled on dry ice from the outside to generate radicals. The polyethylene porous hollow fibers having the obtained radicals were transferred to a glass container, and oxygen in the reaction tube was removed by reduction in pressure to 200 Pa or lower. 55 mL of the reaction solution adjusted to 40° C. was introduced thereto, and the container was left standing for 16 hours. Then, the hollow fibers were washed with methanol and vacuum-dried in a vacuum dryer to obtain 6.10 g of a hollow fiber membrane having a graft rate of 102%. Then, sulfonic acid groups were introduced in the same way as in Example 1 to obtain cation exchange membrane 14. The sulfonic acid group density was 78 mmol/L. The mass of the monomer unit having a sulfonic acid group/the mass of the neutral monomer unit was 1/9.18, and the graft chain density was 0.160 g/mL.

Aggregate removal was evaluated in the same way as in Example 17 except that the cation exchange membrane 14 was used. The results are shown in FIG. 6.

Example 21

In Example 21, cation exchange membrane 15 given below was synthesized, and aggregate removal was evaluated using the AE6F4 antibody in the same way as in Example 17 except that the cation exchange membrane 15 was used. For the preparation of the cation exchange membrane 15, 0.98 g of glycidyl methacrylate were dissolved in 119 mL of methanol, and the solution was bubbled with nitrogen for 30 minutes and used as a reaction solution. 3.02 g (15 cm, 15 fibers) of polyethylene porous hollow fibers having an outside diameter of 3.0 mm, an inside diameter of 2.0 mm, and an average pore size of 0.25 um was placed in a closed container, and air in the container was replaced with nitrogen. Then, the container was irradiated with 25 kGy of γ ray while cooled on dry ice from the outside to generate radicals. The polyethylene porous hollow fibers having the obtained radicals were transferred to a glass container, and oxygen in the reaction tube was removed by reduction in pressure to 200 Pa or lower. 55 mL of the reaction solution adjusted to 40° C. was introduced thereto, and the container was left standing for 16 hours. Then, the hollow fibers were washed with methanol and vacuum-dried in a vacuum dryer to obtain 3.47 g of a hollow fiber membrane having a graft rate of 15%. Then, sulfonic acid groups were introduced in the same way as in Example 1 to obtain cation exchange membrane 15. The sulfonic acid group density was 53 mmol/L. The ratio of the mass of the monomer unit having a sulfonic acid group/the mass of the neutral monomer unit was 1/1.50, and the graft chain density was 0.038 g/mL. The molar ratio between the monomer unit having a sulfonic acid group and the neutral monomer unit was 1/3.2.

Aggregate removal was evaluated in the same way as in Example 17 except that the cation exchange membrane 15 was used. The results are shown in FIG. 6.

Example 22

In Example 22, the cation exchange membrane 1 was used, and the removability of aggregates as well as HCP and protein A was evaluated as to the CRL12445 antibody using antibody solutions prepared from a 15 mmol/L acetate buffer solution (pH 5.0), a 15 mmol/L acetate buffer solution (pH 6.0), and a 15 mmol/L Tris buffer solution (pH 7.0).

The HCP and the protein A were quantified by UV measurement using CHINESE HAMSTER OVARY Host Cell Proteins-3rd Generation ELISA kit from Cygnus Technologies Inc. and PROTEIN A ELISA kit from Cygnus Technologies Inc., respectively, and indicated by ppm as the mass with respect to the mass of the antibody.

The results are shown in FIG. 7.

Example 23

In Example 23, a series of steps (affinity chromatography step, cation exchange chromatography step, and anion exchange chromatography step) were carried out using the CRL12445 antibody without buffer replacement.

(Affinity Chromatography Step)

In the affinity chromatography step according to Example 23, the operation was performed at a flow rate of 20 mL/min. First, a column packed with 58 mL of MabSelect Sure was equilibrated with 150 mL of a phosphate buffer solution (20 mmol/L sodium phosphate+150 mmol/L NaCl (pH 8.0)), and a culture supernatant containing the CRL12445 antibody was added to the column to adsorb 1.22 g of the antibody thereto. Next, the column was washed by the injection of 300 mL of a phosphate buffer solution (20 mmol/L sodium phosphate+150 mmol/L NaCl (pH 8.0)) and further the injection of 180 mL of a Tris/acetate buffer solution (100 mmol/L (pH 8.0)). Then, the antibody was eluted from the column by the injection of 300 mL of a 25 mmol/L acetate buffer solution (pH 3.4) as an elution buffer to collect only a fraction containing the eluted antibody. The pH of the eluate was adjusted to 6.0 by the addition of a 1 mol/L Tris buffer solution to obtain an antibody solution. The obtained antibody solution had an electrical conductivity of 1.7 mS/cm. The obtained antibody solution was mixed with an antibody solution having the same solution composition thereas and containing a large amount of aggregates to prepare an antibody solution for use in the cation exchange chromatography step mentioned later. In the antibody solution, the ratio of the aggregate (1) was 1.35%, the ratio of the aggregate (2) was 0.77%, and the ratio of the monomer was 97.87%. The content of the HCP was 230 ppm, and the content of the protein A was 3 ppm. The results are shown in FIG. 8.

(Cation Exchange Chromatography Step)

In the cation exchange chromatography step according to Example 23, the cation exchange membrane 1 (volume: 0.3 mL) was used. The amount of the antibody solution added to the cation exchange membrane 1 was 50 mL (concentration: 6.5 mg/mL), and the flow rate was 1.8 mL/min. After injection of the antibody solution to the cation exchange membrane 1, the cation exchange membrane 1 was washed by the injection of 12 mL of a buffer (pH 6.0) having the same composition as that of the antibody solution at a flow rate of 1.8 mL/min. 60 mL of a solution was recovered by the flow-through step and the washing step. The same operation as above was repeated twice, and the recovered solution was analyzed by size exclusion chromatography (SEC) and ELISA. As a result, the contents of the aggregate components, the HCP and the protein A were decreased. The results are shown in FIG. 8.

(Anion Exchange Chromatography Step)

In the anion exchange chromatography step according to Example 23, an anion exchange membrane having a volume of 0.25 mL (QyuSpeed D, Asahi Kasei Medical Co., Ltd.) was used. The antibody solution recovered in the cation exchange chromatography step was adjusted to pH 7.8 by the addition of a 1 mol/L Tris buffer solution and consequently had an electrical conductivity of 1.7 mS/cm. Then, the antibody solution was contacted with QyuSpeed D. The amount of the antibody solution added to QyuSpeed D was 165 mL (concentration: 4.5 mg/mL), and the flow rate was 1.5 mL/min. After injection of the antibody solution to QyuSpeed D, QyuSpeed D was washed by the injection of 10 mL of a buffer (pH 7.8) having the same composition as that of the antibody solution at a flow rate of 1.5 mL/min. 175 mL in total of a solution was recovered by the flow-through step and the washing step. The recovered solution was analyzed by size exclusion chromatography (SEC) and ELISA. As a result, the contents of the aggregate components, the HCP and the protein A were decreased. The results are shown in FIG. 8.

Example 24

In Example 24, a series of steps (affinity chromatography step, virus inactivation step at low pH, cation exchange chromatography step, and anion exchange chromatography step) were performed using the CRL12445 antibody without buffer replacement.

(Affinity Chromatography Step)

In the affinity chromatography step according to Example 24, the operation was performed at a flow rate of 20 mL/min. First, a column packed with 58 mL of MabSelect Sure was equilibrated with 150 mL of a phosphate buffer solution (20 mmol/L sodium phosphate+150 mmol/L NaCl (pH 8.0)), and a culture supernatant containing the CRL12445 antibody was added to the column to adsorb 1.22 g of the antibody thereto. Next, the column was washed by the injection of 300 mL of a phosphate buffer solution (20 mmol/L sodium phosphate+150 mmol/L NaCl (pH 8.0)) and further the injection of 180 mL of a Tris/acetate buffer solution (100 mmol/L (pH 8.0)). Then, the antibody was eluted from the column by the injection of 300 mL of a 25 mmol/L acetate buffer solution (pH 3.4) as an elution buffer to collect only a fraction containing the eluted antibody. The obtained antibody solution was adjusted to pH 2.7 by the addition of 1 mol/L hydrochloric acid and left standing for 2 hours to carry out virus inactivation treatment. Then, the pH of the resulting solution was adjusted to 6.0 by the addition of a 1 mol/L Tris buffer solution to obtain an antibody solution. The obtained antibody solution had an electrical conductivity of 2.7 mS/cm and was used as an antibody solution for use in the cation exchange chromatography step mentioned later. In the antibody solution, the ratio of the aggregate (1) was 1.70%, the ratio of the aggregate (2) was 1.89%, and the ratio of the monomer was 96.41%. The content of the HCP was 307 ppm, and the content of the protein A was 3 ppm. The results are shown in FIG. 8.

(Cation Exchange Chromatography Step)

In the cation exchange chromatography step according to Example 24, the cation exchange membrane 1 (volume: 0.72 mL) was used. The amount of the antibody solution added to the cation exchange membrane 1 was 125 mL (concentration: 7.2 mg/mL), and the flow rate was 4.4 mL/min. After injection of the antibody solution to the cation exchange membrane 1, the cation exchange membrane 1 was washed by the injection of 15 mL of a buffer (pH 6.0) having the same composition as that of the antibody solution at a flow rate of 4.4 mL/min. 135 mL of a solution was recovered by the flow-through step and the washing step. The recovered solution was analyzed by size exclusion chromatography (SEC) and ELISA. As a result, the contents of the aggregate components, the HCP and the protein A were decreased. The results are shown in FIG. 8.

(Anion Exchange Chromatography Step)

In the anion exchange chromatography step according to Example 24, an anion exchange membrane having a volume of 0.25 mL (QyuSpeed D, Asahi Kasei Medical Co., Ltd.) was used. The antibody solution recovered in the cation exchange chromatography step was adjusted to pH 8.0 by the addition of a 1 mol/L Tris buffer solution and consequently had an electrical conductivity of 2.7 mS/cm. Then, the antibody solution was contacted with QyuSpeed D. The amount of the antibody solution added to QyuSpeed D was 132 mL (concentration: 5.6 mg/mL), and the flow rate was 1.5 mL/min. After injection of the antibody solution to QyuSpeed D, QyuSpeed D was washed by the injection of 10 mL of a buffer (pH 8.0) having the same composition as that of the antibody solution at a flow rate of 1.5 mL/min. 142 mL in total of a solution was recovered by the flow-through step and the washing step. The recovered solution was analyzed by size exclusion chromatography (SEC) and ELISA. As a result, the contents of the aggregate components, the HCP and the protein A were decreased. The results are shown in FIG. 8.

Example 25

In Example 25, the same operation as in Example 24 was performed except that Mustang Q having a volume of 0.18 mL (Pall Corporation) was used in the anion exchange chromatography step, and the treatment was performed at a flow rate of 0.9 mL/min. The results are shown in FIG. 8.

Example 26

In Example 26, the CRL12445 antibody was used, and after an affinity chromatography step and a virus inactivation step at low pH, a cation exchange chromatography step and an anion exchange chromatography step were carried out, without pH adjustment therebetween, by directly connecting a cation exchange chromatographic matrix with an anion exchange chromatographic matrix.

(Affinity Chromatography Step)

In the affinity chromatography step according to Example 26, the operation was performed at a flow rate of 20 mL/min. First, a column packed with 58 mL of MabSelect Sure was equilibrated with 150 mL of a phosphate buffer solution (20 mmol/L sodium phosphate+150 mmol/L NaCl (pH 8.0)), and a culture supernatant containing the CRL12445 antibody was added to the column to adsorb 1.35 g of the antibody thereto. Next, the column was washed by the injection of 300 mL of a phosphate buffer solution (20 mmol/L sodium phosphate+150 mmol/L NaCl (pH 8.0)) and further the injection of 180 mL of a Tris/acetate buffer solution (100 mmol/L (pH 8.0)). Then, the antibody was eluted from the column by the injection of 300 mL of a 25 mmol/L acetate buffer solution (pH 3.4) as an elution buffer to collect only a fraction containing the eluted antibody. The obtained antibody solution was adjusted to pH 2.7 by the addition of 1 mol/L hydrochloric acid and left standing for 2 hours to carry out virus inactivation treatment. Then, the pH of the resulting solution was adjusted to 5.0 by the addition of a 1 mol/L Tris buffer solution. The composition of the antibody solution is shown in FIG. 9. In addition to the antibody solution of pH 5.0, antibody solutions adjusted to pH 6.0, 7.0, and 8.0 were further obtained. The obtained antibody solutions had concentrations of 7.1 mg/mL, 7.1 mg/mL, 7.1 mg/mL, and 7.0 mg/mL and electrical conductivities of 2.6, 2.7, 2.7, and 2.7 mS/cm, respectively, and were used as antibody solutions for use in the ion exchange chromatography step mentioned later.

(Ion Exchange Chromatography Step)

In the ion exchange chromatography step according to Example 26, the cation exchange membrane 1 having a volume of 0.30 mL and an anion exchange membrane having a volume of 0.25 mL (QyuSpeed D, Asahi Kasei Medical Co., Ltd.) were connected in series and used. After the affinity chromatography step at a flow rate of 1.5 mL/min, the antibody solution of each pH was injected to the membranes, and the membranes were washed with 15 mL of a buffer having the same composition as that of the antibody solution at a flow rate of 1.5 mL/min. The purification results are shown in FIG. 9.

The invention claimed is:

1. A purification method for purifying a physiologically active substance from a mixed solution containing impurities and the physiologically active substance, comprising
contacting the mixed solution with a cation exchange chromatographic matrix for biomolecule purification, wherein the cation exchange chromatographic matrix comprises:
a base material, and
a copolymer with one monomer unit having at least a sulfonic acid group, the copolymer being on a graft chain immobilized on the base material wherein:
the copolymer forms substantially no cross-linked structure, and the copolymer comprises neither acrylamide nor an acrylamide derivative as a monomer unit, or comprises acrylamide or an acrylamide derivative as a monomer unit at a mass percent of 10% or less based on all monomer units of the copolymer;
the ratio of the mass of the copolymer to the mass of the base material is 5% or more and 200% or less;
the density of the sulfonic acid group is higher than 30 mmol/L and 200 mmol/L or lower;
the mixed solution is contacted with the matrix in a flow-through mode; and
a mass of graft chain per the cation exchange chromatographic matrix volume is 0.03 g/mL or larger and 0.25 g/mL or smaller, wherein the mass of graft chain per the cation exchange chromatographic matrix volume is represented by the following expression:

$$sg(g/mL)=(w_2-w_0)/v_1$$

wherein $w_2$ is the mass of the cation exchange chromatographic matrix obtained as a final product, $v_1$ is the volume of the cation exchange chromatographic matrix obtained as the final product, and $w_0$ is the mass of the base material before introduction of the graft chain.

2. The purification method according to claim 1, wherein the pH of the mixed solution is 4.0 or higher and 10.0 or lower.

3. The purification method according to claim 1, wherein the physiologically active substance is a monomer of an antibody protein.

4. The purification method according to claim 1, wherein the impurities include dimeric and higher aggregates of the antibody protein.

5. The purification method according to claim 1, wherein the recovery rate of the physiologically active substance is 80% or more.

6. The purification method according to claim 1, wherein 100 mg or more of the antibody protein including the monomer and the aggregates is purified per mL of the cation exchange chromatographic matrix for biomolecule purification.

7. The purification method according to claim 1, wherein the ratio of the aggregates is reduced by 50% or more when a solution of the antibody protein including the monomer and the aggregates is purified.

8. The purification method according to claim 1, further comprising performing purification using an anion exchange chromatographic matrix before or after the purification using the cation exchange chromatographic matrix.

9. The purification method according to claim 8, wherein the anion exchange chromatographic matrix is in a membrane form.

10. The purification method according to claim 8, wherein the purification using an anion exchange chromatographic matrix is a flow-through mode.

11. The purification method according to claim 8, further comprising performing affinity chromatography before the purification using the cation exchange chromatographic matrix and the purification using the anion exchange chromatographic matrix.

12. The purification method according to claim 8, wherein buffer replacement is not performed in a series of purifications.

13. The purification method according to claim 11, wherein the affinity chromatography is carried out in a bind and elute mode, and the physiologically active substance is eluted with a buffer consisting of a monovalent acid in the elution.

14. The purification method according to claim 13, wherein the electrical conductivity of the buffer consisting of a monovalent acid is 10.0 mS/cm or lower.

15. The purification method according to claim 11, further comprising adjusting the pH of the mixed solution to 4.0 or lower after performing the affinity chromatography.

16. The purification method according to claim 8, wherein the electrical conductivity of the mixed solution containing the physiologically active substance is 10 mS/cm or lower in a series of purifications.

17. The purification method according to claim 1, wherein the molar percent of the monomer unit having the sulfonic acid group in the copolymer is smaller than the molar percent of a neutral monomer unit having no charge.

18. The purification method according to claim 1, wherein the mass percent of the monomer unit having the sulfonic acid group in the copolymer is smaller than the mass percent of a neutral monomer unit having no charge.

19. The purification method according to claim 1, wherein the monomer unit having the sulfonic acid group is a glycidyl methacrylate derivative.

20. The purification method according to claim 17, wherein the neutral monomer unit comprises at least a hydrophilic monomer unit derived from (meth)acrylate compounds selected from the group consisting of 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 4-hydroxybutyl acrylate, 4-hydroxybutyl methacrylate, 2-(dimethylamino)ethyl acrylate, and 2-(dimethylamino)ethyl methacrylate, and mixtures thereof, and the molar ratio of the hydrophilic monomer unit to the neutral monomer unit in the copolymer is 50% or more.

21. The purification method according to claim 18, wherein the neutral monomer unit comprises at least a hydrophilic monomer unit derived from (meth)acrylate compounds selected from the group consisting of 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, 4-hydroxybutyl acrylate, 4-hydroxybutyl methacrylate, 2-(dimethylamino)ethyl acrylate, and 2-(dimethylamino)ethyl methacrylate, and mixtures thereof, and the ratio of the mass of the hydrophilic monomer unit to the total mass of the neutral monomer unit in the copolymer is 50% or more.

22. The purification method according to claim 1, wherein the cation exchange chromatographic matrix contains no carboxyl group, or has a density of a carboxyl group lower than the density of the sulfonic acid group.

23. The purification method according to claim 1, wherein the base material is in a membrane form.

24. The purification method according to claim 1, wherein the cation exchange chromatographic matrix for biomolecule purification is structured and configured for antibody protein purification.

25. The purification method according to claim 2, wherein the pH of the mixed solution is 5.0 or higher and 7.0 or lower.

26. The purification method according to claim 6, wherein 500 mg or more of the antibody protein including the monomer and the aggregates is purified per mL of the cation exchange chromatographic matrix for biomolecule purification.

* * * * *